United States Patent [19]

Bader et al.

[11] Patent Number: 5,938,904
[45] Date of Patent: Aug. 17, 1999

[54] SEPARATION OF CHARGED PARTICLES BY A SPATIALLY AND TEMPORALLY VARYING ELECTRIC FIELD

[75] Inventors: Joel S. Bader; Jonathan M. Rothberg, both of Branford, Conn.; Michael W. Deem, Cambridge, Mass.; Gregory T. Mulhern, Branford; Gregory T. Went, Madison, both of Conn.

[73] Assignee: CuraGen Corporation, New Haven, Conn.

[21] Appl. No.: 08/623,346

[22] Filed: Mar. 27, 1996

[51] Int. Cl.$^6$ .......................... G01N 27/26; G01N 27/447
[52] U.S. Cl. .............................................. 204/450; 204/600
[58] Field of Search .................................. 204/450, 451, 204/547, 601, 602, 643, 600

[56] References Cited

U.S. PATENT DOCUMENTS

| | | | |
|---|---|---|---|
| 4,908,112 | 3/1990 | Pace | 204/601 X |
| 5,126,022 | 6/1992 | Soane et al. | 204/458 |
| 5,171,534 | 12/1992 | Smith et al. | 204/612 |
| 5,192,450 | 3/1993 | Heyman | 210/748 |
| 5,374,527 | 12/1994 | Grossman | 204/451 |
| 5,593,565 | 1/1997 | Ajdari et al. | 204/643 |

FOREIGN PATENT DOCUMENTS

| | | |
|---|---|---|
| 0376611 A3 | 7/1990 | European Pat. Off. . |
| 0645169 A1 | 3/1995 | European Pat. Off. . |
| 645169 | 3/1995 | European Pat. Off. . |

OTHER PUBLICATIONS

Jullette Rousselet et al, "Directional Motion of Brownian Particles Induced by a Periodic Asymmetric Potential" Nature, vol. 370 (Aug. 11, 1994) 446–488.

Astumian, 1997 No Month Available, "Thermodynamics and kinetics of a Brownian motor", Science 276:917–922.

Panofsky and Phillips, 1962 No Month Available, *Classical Electricity and Magnetism* (Addison–Wesley Publishing Company, Inc., Massachusetts) chapters 1–4.

Abramowitz et al., No Month Available. 1972, *Handbook of Mathematical Functions* (Dover Publishers Inc., New York) pp. 297–299.

Ajdari et al., No Month Available. 1991, "Free-flow electrophoresis with trapping by a transverse inhomogeneous field", *Proc. Natl. Acad. Sci. USA* 88:4468–4471.

(List continued on next page.)

*Primary Examiner*—William H. Beisner
*Assistant Examiner*—John S. Starsiak, Jr.
*Attorney, Agent, or Firm*—Pennie & Edmonds LLP

[57] ABSTRACT

This invention relates to a method and device for separating charged particles according to their diffusivities in a separation medium by means of a spatially and temporarily varying electric potential. The method is particularly suited to sizing and separating DNA fragments, to generating DNA fragment length polymorphism patterns, and to sequencing DNA through the separation of DNA sequencing reaction products. The method takes advantage of the transport of charged particles subject to an electric potential that is cycled between an off-state (in which the potential is flat) and one or more on-states, in which the potential is preferably spatially periodic with a plurality of eccentrically shaped stationary potential wells. The potential wells are at constant spatial positions in the on-state. Differences in liquid-phase diffusivities lead to charged particle separation. A preferred embodiment of the device is microfabricated. A separation medium fills physically defined separation lanes in the device. Electrodes deposited substantially transverse to the lanes create the required electric potentials. Advantageously, injection ports allow sample loading, and special gating electrodes focus the sample prior to separation. The effects of thermal gradients are minimized by placing the device in contact with a thermal control module, preferably a plurality of Peltier-effect heat transfer devices. The small size of a microfabricated device permits rapid separation in a plurality of separation lanes.

46 Claims, 16 Drawing Sheets

OTHER PUBLICATIONS

Avallone et al., eds., No Month Available. 1987, *Marks' Standard Handbook for Mechanical Engineers* (McGraw–Hill, New York) pp. 15–19.

Barron et al., No Month Available. 1994, "A transient entanglement coupling mechanism for DNA separeation by capillary electrophoresis in ultradilute polymer solutions", *Electrophoresis* 15:597–615.

Barron et al., No Month Available. 1993, "Capillary electrophoresis of DNA in uncross–linked polymer solutions", *J. Chromatogr. A* 652:3–16.

Bier et al., No Month Available. 1996, "Biasing Brownian motion in different directions in a 3–state fluctuating potential and an application for the separation of small particles", *Physical Review Letters* 76:4277–4280.

Burlatsky et al., No Month Available. 1993, "Influence of solid friction on polymer relaxation in gel electrophoresis", *Science* 260:1782–1784.

Chauwin et al., No Month Available. 1994, "Force–free motion in asymmetric structures: a mechanism without diffusive steps", *Europhys. Lett.* 27:421–426.

Derenyi et al., No Month Available. 1995, "Cooperative transport of brownian particles", *Physical Review Letters* 75:374–377.

Doi et al., No Month Available, 1986, *The Theory of Polymer Dynamics* (Clarendon Press, Oxford) pp. 24–25 and 298–301.

Drmanac et al., No Month Available. 1993, "DNA sequence determination by hybridation: a strategy for efficient large–scale sequencing", *Science* 260:1649.

Effenhauser et al., No Month Available. 1993, "Glass chips for high–speed capillary electrophoresis separations with submicrometer plate heights", *Anal. Chem.* 65:2637–2642.

Elston et al., No Month Available. 1996, "Numerical and analytical studies of nonequilibrium fluctuation–induced transport processes", *J. Stat. Phys.* 83:359–383.

Faucheux et al., No Month Available. 1995, "Optical thermal ratchet", *Physical Review Letters* 74:1504–1507.

Harrison et al., No Month Available 1993, "Micromaching a miniaturized capillary electrophoresis–based chemical analysis system on a chip", *Science* 261:895–897.

Harrison et al., No Month Available 1992, "Capillary electrophoresis and sample injection systems integrated on a planar chip", *Anal. Chem.* 64:1926–1932.

Holmes and Stellwagen, No Month Available 1991, "Estimation of polyacrylamide gel pore size from Ferguson plots of normal and anomalously migrating DNA fragments", *Electrophoresis* 12:253–263.

Huang et al., No Month Available 1992, "DNA sequencing using capillary array electrophoresis", *Anal. Chem.* 64:2149–2154.

Huber et al., No Month Available 1993, "High–resolution liquid chromatography of DNA fragments on non–porous poly(styrene–divinylbenzene) particles", *Nucl. Acids Res.* 21:1061–1066.

Jackman et al., "Fabrication of submicrometer features on curved substrates by microcontact printing", No Month Available 1995, *Science* 269:664–666.

Jacobson et al., No Month Available 1992, "Development of resonance ionization spectroscopy for DNA sequencing and genome mapping", *Anal. Chem.* 64:315–328.

Jacobson et al., No Month Available 1994, "Effects of injection schemes and column geometry on the performance of microchip electrtophoreis devices", *Anal. Chem.* 66:1107–1113.

Julicher et al., No Month Available 1995, "Cooperative molecular motors", *Physical Review Letters* 75:2618–2621.

Kim et al., No Month Available 1994, "Separation of nucleic acids by capillary electrophoresis in cellulose solutions with mono–and bis–intercalating dyes", *Anal. Chem.* 66:1168–1174.

Kostichka et al., No Month Available 1992, "High speed automated DNA sequencing in ultrathin slab gels", *Bio/Technology* 10:78–81.

Kumar et al., No Month Available 1994, "Patterning self––assembled monolayers: applications in materials science", *Langmuir* 10:1498–1511.

Maxam et al., No Month Available 1977, "A new method for sequencing DNA", *Proc. Natl. Acad. Sci. USA* 74:560–564.

Navin, et al., No Month Available 1994, "Variable frequency modulation in DNA separations using field inversion capillary gel electrophoresis", *Anal. Chem.* 66:1179–1182.

Olson, No Month Available 1993, "The human genome project", *Proc. Natl. Acad. Sci. USA* 90:4338–4344.

Press et al., No Month Available 1992, *Numerical Recipes in C*, 2nd ed. (Cambridge Univ. Press, New York) pp. 394–431, 753–787.

Rousselet et al., No Month Available 1994, "Directional motion of brownian particles induced by a periodic asymetric potential", *Nature* 370:446–448.

Sanger et al., No Month Available 1977, "DNA sequencing with chain–terminating inhibitors", *Proc. Natl. Acad. Sci. USA* 74:5463–5467.

Schulman, No Month Available 1981, *Techniques and Applications of Path Integration* (John Wiley & Sons, New York) pp. 53–64.

Simon et al., No Month Available 1992, "Escape and synchronization of a brownian particle", *Physical Review Letters* 68:3375–3378.

Smith, No Month Available 1993, "The future of DNA sequencing", *Science* 262:530.

Volkmuth et al., No Month Available 1992, "DNA electrophoresis in microlithographic arrays", *Nature* 358:600–602.

Wax, ed, No Month Available 1954, *Selected Papers on Noise and Stochastic Processes* (Dove Publishers, New York) pp. 3–33.

Weast, ed., No Month Available 1987, *Handbook of Chemistry and Physics* (Chemical Rubber Publishing Co., Boca Raton, FL), p. D156.

Wood et al., No Month Available 1995, "Sequence verification of human creatine kinase (43 kDa) isozymes by high–resolution tandem mass spectroscopy", *Proc. Natl. Acad. Sci. USA* 92:11451.

Woolley et al., No Month Available 1994, "Ultra–high speed DNA fragment separartions using microfabricated capillary array electrophoresis chips", *Proc. Natl. Acad. Sci. USA* 91:11348–11352.

Xia et al., No Month Available. 1995, "Use of controlled reactive spreading of liquid alkanethiol on the surface of gold to modify the size of features produced by microcontact printing", *J. Am. Chem. Soc.* 117:3274–3275.

SEPARATION OF CHARGED PARTICLES BY A SPATIALLY AND TEMPORALLY VARYING ELECTRIC FIELD

A portion of the disclosure of this patent document contains material which is subject to copyright protection. The copyright owner has no objection to the facsimile reproduction by any one of the patent disclosure, as it appears in the Patent and Trademark Office patent files and records, but otherwise reserves all copyright rights whatsoever.

This invention was made with United States Government support under award number 70NANB5H1036 awarded by the National Institute of Standards and Technology. The United States Government has certain rights in the invention.

1. FIELD OF THE INVENTION

This invention relates to a method and apparatus for the separation of charged particles in a medium according to the differences of the diffusivities of the particles in the medium by use of a spatially and temporally varying electric potential. Particularly, the invention relates to a method and apparatus for separation of charged biopolymers in a liquid medium, and more particularly to a method and apparatus for the separation of single-stranded or double-stranded DNA fragments for DNA sequencing and for general fragment length determination.

2. BACKGROUND OF THE INVENTION

Separations of charged particles, in particular physical mixtures of chemical species, are important analytical operations. Relevant chemical species include non-biological charged species, such as synthetic polymers, and biological charged species, such as DNA, RNA, or proteins (A. J. Kostichka et al., 1992, *Bio/Technology* 10:78). Separations of mixtures of DNA fragments are particularly important.

For example, the Human Genome Project demonstrates the need for powerful DNA fragment separation methods and apparatus. This project is an ambitious, international effort to improve human genetic maps, to sequence fully the genomes of humans and several model organisms by 2006, and to develop computational tools for storing and accessing the burgeoning information. This project requires a technological infrastructure capable of supplying high-quality sequence information in a rapid and cost-effective manner.

To sequence fully the human genome, which has approximately $3 \times 10^9$ base pairs, by the year 2006 requires roughly 100 times beyond the total, current worldwide DNA sequencing capacity (M. V. Olson, 1993, *Proc. Natl. Acad. Sci. USA* 90:4338). Existing DNA sequencing methods, for example, mass spectrometry (T. D. Wood et al., 1995, *Proc. Natl. Acad. Sci. USA* 92:11451), sequencing by hybridization (R. Drmanac et al., 1993, *Science* 260:1649), chromatography (C. G. Huber et al., 1993, *Nucl. Acids Res.* 21:1061), acoustophoresis (J. S. Heyman, U.S. Pat. No. 5,192,450), and electrophoresis, are generally inadequate to meet this sequencing goal.

The above methods have various drawbacks. Mass spectrometry requires an expensive mass spectrometer. Because of this cost, it is unlikely that this method will have widespread applicability. Sequencing by hybridization is still relatively new and untested. Liquid chromatography is capable of performing rapid separation of double-stranded DNA fragments, but is limited by poor resolution. The single-base resolution necessary for sequencing has only been demonstrated for fragments smaller than 150 base pairs. In acoustophoresis, acoustic waves push fragments through a liquid medium. This method is limited by the similarity in the acoustic properties of DNA fragments of similar lengths, preventing effective separation.

Electrophoresis remains the most common method by far for DNA sequencing. All conventional electrophoretic methods are generally similar (F. Sanger et al., 1977, *Proc. Natl. Acad. Sci. USA* 74:5463; L. M. Smith, 1993, *Science* 262:530). A DNA sample is generally first amplified, that is the DNA chains are made to replicate, usually by the polymerase chain reaction ("PCR"). Next, from the amplified sample, chain terminating DNA polymerase reactions (first described by Sanger et al.) produce nested sets of DNA fragments labeled with one of four unique fluorescent dyes conjugated with one of the four chain terminating bases (either ddATP, ddCTP, ddGTP, or ddTTP). In a related method, the chains are cleaved by chemical means to produce a similar set of labeled fragments (M. Maxam et al., 1977, *Proc. Natl. Acad. Sci. USA* 74:560). These fragments are then separated according to their molecular size by a variety of electrophoretic techniques, and the unique dye labeling each chain terminating base is detected by its fluorescence. The DNA base sequence is reconstructed from the detected pattern of chain fragments.

The accuracy required in DNA fragment size determination depends on the application. For example, DNA sequencing reactions produce a mixture, called a "ladder," of fragments with lengths separated by single bases and require exact length determination. Other applications produce greater differences between the fragment lengths, and methods that provide rapid sizing, but not necessarily exact length information, are valuable. Typical of such applications are the generation of patterns of restriction fragment length polymorphism ("RFLP"), genotyping, linkage analysis, microsatellite analysis and other fragment analysis application.

In an electrophoretic separation, the DNA molecules are separated according to their rates of migration in an electric field. The electric driving force is proportional to the net charge of the molecule. For a uniformly charged biopolymer such as DNA, the driving force is proportional to the number of base pairs in the DNA fragment. Since in a material obeying Stokes' Law, such as a liquid, the friction coefficient is also proportional to the number of base pairs, the DNA fragments have electrophoretic drift velocities that are nearly identical and independent of fragment length. This means electrophoretic separation of DNA fragments is difficult in liquids or other media obeying Stokes' Law.

Therefore, instead of liquid media, cross-linked gels and uncross-linked polymer solutions are universally used in electrophoretic DNA separations. In these media, DNA does not obey Stokes' law, since the electrophoretic drift velocity decreases with increasing length or molecular weight. Thus, electrophoretic separation of biopolymers is ordinarily performed in a polymeric gel, such as agarose or polyacrylamide, in which separation of biopolymers with similar electric charge densities, such as DNA or RNA, depends on molecular weight. The non-Stokes' law dependence of the friction coefficient on the fragment size in a gel permits electrophoretic separation of DNA fragments of different lengths. Biopolymer fragments, therefore, exit the device in size order from small to large.

In a prevalent configuration, the electrophoretic gel is disposed as a thin sheet between two flat, parallel, rectangular glass plates. An electric field is established along the long axis of the rectangular configuration, and molecular migration is arranged to occur simultaneously in several paths, or "lanes," parallel to the electric field. To ensure high separation resolution, it is advantageous that gel throughout a migration lane be as uniform as possible (or homogeneous like a liquid) and for the lanes to be sufficiently separated to be clearly distinguishable.

It has proven difficult to make, or "to cast," uniform gels with uniform transport properties. One major problem is uneven gel shrinkage due to cross-linking during gel polymerization. The problems in casting a uniform gel also lead to difficulties in producing a uniform and reproducible loading region, into which sample mixtures are placed prior to separation. It is generally accepted that a separation medium with more reproducible transport properties (i.e., more like a homogeneous liquid) would have great utility.

In addition to high separation resolution, demands for more rapid electrophoresis have created additional problems for gel manipulation. Rapid electrophoresis is desirable for rapid, high capacity biopolymer analysis. This requires, primarily, stronger electric fields that exert greater forces on migrating molecules in order to move them at greater velocities. However, higher fields, voltages, and velocities lead to increased resistive heating in the gel, and consequently, significant thermal gradients in the gel. Such thermal gradients cause additional gel non-uniformities that further impair separation resolution.

To maintain resolution at higher voltages, ever smaller gel geometries are used so that damaging heat may be more readily conducted away. Thus, electrophoresis has been described in geometries where the parallel glass plates are spaced from 25 to 150 $\mu$m apart, instead of the usual spacings which are typically greater than 1000 $\mu$m (A. J. Kostichka et al., 1992, *Bio/Technology* 10:78). It has proven even more difficult to cast uniform gels of such thinness and to assure long, parallel, narrow, and closely spaced migration lanes in so thin a sheet.

In turn, to overcome these difficulties in thin gels, physical separation means have been used to keep lanes distinct. These separation means create yet a further set of problems. In one such method for producing physically distinct lanes, arrays of capillary tubes with diameters down to 100 $\mu$m have been used (X. C. Huang et al., 1992, *Anal. Chem.* 64:2149). These capillary arrays are difficult to cast with uniform gels and difficult to load with samples of fragments. Easy loading is advantageous to minimize the time and cost of the separation setup, which is often labor-intensive. An alternative is to use a dilute polymer solution instead of a gel in each capillary (P. D. Grossman, U.S. Pat. No. 5,374,527). However, single base resolution in such solutions has been limited to DNA chains with fewer than 200 bases and loading the capillaries with samples remains difficult (A. E. Barron et al., 1993, *J. Chromatogr. A* 652:3; A. E. Barron et al., 1994, *Electrophoresis* 15:597; and Y. Kim et al., 1994, *Anal. Chem.* 66:1168). Other alternatives include producing physically distinct lanes by microfabrication of channels in an electrophoretic device (D. J. Harrison et al., 1992, *Anal. Chem.* 64:1926 and D. J. Harrison et al., 1993, *Science* 261:895). Electrodes can be deposited to provide precise control of the electrophoretic field (G. T. A. Kovacs et al., 1990, European Patent 0 376 611 A3 and D. S. Soane et al., U.S. Pat. No. 5,126,022). In another alternative to migration through gels, optical microlithography has been used to fabricate a quasi-two-dimensional array of migration obstacles for the electrophoretic separation of DNA (W. D. Volkmuth et al., 1992, *Nature* 358:600).

Small lane size coupled with the desirability of separating many samples in many migration lanes at once creates conflicting physical requirements. Simultaneous detection of fragments migrating in multiple lanes requires a spatially compact disposition of the migration lanes in order that all the lanes can be observed at once by a spectrograph of limited aperture. However, loading samples into migration lanes prior to separation requires physical access to the migration lanes that is easier and more rapid for widely spaced lanes. Conventional, flat-plate techniques have only straight, parallel lanes and cannot accommodate these divergent requirements.

Such problems with prior gel-based electrophoretic separation methods have motivated a search for new separation methods. A non-electrophoretic method for separation of particles that are electrically polarizable, but not charged, is based on differences in diffusivities in liquid of the particles. Only mega-base size DNA fragments have sufficient polarizability to be separated by this method (A. Ajdari et al., 1991, *Proc. Natl. Acad. Sci. USA* 88:4468; J. Rousselet et al., 1994, *Nature* 370:446; and J. F. Chauwin et al, 1994, *Europhys. Lett.* 27:421). This method uses an electric field that is periodic but asymmetric in space, substantially transverse to the direction of separation, and cycles temporally from on to off. When the asymmetric field is turned on, it attracts and traps polarizable particles into a series of spatially periodic attractive regions according to the known laws of electrostatics. When the potential is turned off, however, the particles are free to diffuse. Since smaller particles diffuse more rapidly, the cycling electric field causes a size separation of polarizable particles.

The polarization-based device is suited for separating particles on the order of the size of viruses, and may also be able to effect the separation of mega-base fragments of DNA, such as entire chromosomes (J. Rousselet et al., 1994, *Nature* 370:446). This particle size limitation is due to the requirement that the particles to be separated have polarizabilities sufficiently large to be attracted by fields that can be realistically created in a liquid. Since the attractive force varies as the square of the electric field, high voltages are needed. Separation of DNA fragments of a few 100's of bases in length, the sizes commonly produced by sequencing reactions or by RFLPS, is out of reach of this or similar polarization-based devices due to practical limits on electric field strength and voltages.

All the foregoing technical problems have hindered creation of a machine for rapid, concurrent analysis of large numbers of biopolymer samples at low cost and with minimal human intervention. The need for such a machine is widely felt in many areas of biology such as, for example, biological research, the Human Genome Project, the biotechnology industry, and clinical diagnosis.

Citation of references hereinabove shall not be construed as an admission that such reference is prior art to the present invention.

3. SUMMARY OF THE INVENTION

It is one object of the method and apparatus of this invention to provide convenient and efficient separation of charged particles which overcomes the problems in the prior art. The particles to be separated may be charged either positively or negatively. In particular, the charged particles separated can be biopolymer fragments, such as single-stranded or double-stranded DNA.

It is another object of the method and apparatus of this invention that separation is accomplished with a spatially and temporally varying electric potential. The potential has a plurality of eccentrically-shaped potential wells that trap the charged particles when the potential is relatively strong. Separation occurs as particles diffuse differentially from well to well, based on differences in diffusivity in the separation medium, when the potential is sufficiently weak (or off). It is an advantage that there is no overall electric potential difference along the line of particle separation.

It is an advantage of the method and apparatus that charged particles interact with an electric potential. This is a stronger interaction, for readily obtainable electric fields, than the weaker interaction between polarizable particles and an inhomogeneous electric field, which depends on the square of the electric field strength, the degree of spatial inhomogeneity of the field, and the polarizability of the particles.

It is an advantage of the method and apparatus of this invention that the form of the electric potential of this invention separates charged particles solely on the basis of their diffusivity in the separation medium. Thereby, this invention can separate DNA fragments in liquid or Stokes' Law medium, which is not possible for conventional electrophoresis. Further, more rapid DNA separation is possible, as liquid diffusivities are larger than gel diffusivities. However, the method and apparatus of the invention are not limited to liquid separation media.

It is an advantage of the method and apparatus that a liquid medium may be used instead of a gel-based medium. When using a liquid medium, the method and apparatus of the invention is free of many of the limitations of gel-based media, including, for example, difficulty in loading gels in small geometries, gel non-uniformities due to shrinkage, electro-endosmosis, and inhomogeneous gel casting. Because a liquid separation medium is substantially uniform, more reproducible separation is possible and non-uniformities in the separation medium are minimized. Further, the apparatus is quickly reusable. Samples may be removed by applying a uniform high voltage. Alternatively, the liquid separation medium may be quickly flushed, and the apparatus then washed with cleaning solution and refilled with fresh liquid medium.

It is an advantage that the apparatus of the invention can be of small scale suitable for microfabrication. The small scale results in high throughput. A small scale results in efficient heat transfer, reducing separation medium non-uniformities due to local heating. Further, the smaller the apparatus the more rapid the separation. Moreover, the apparatus is suitable for low cost microfabrication. Multiple lanes can be fabricated on a single one centimeter square substrate. A separation module according to this invention can be integrated with sample preparation and fragment detection apparatus. A loading zone can be fabricated on the separation module including electrodes generating a loading potential for localizing loaded samples into a compact volume prior to separation.

It is an advantage of the method and apparatus of the invention that operating parameters can be adjusted to the sizes of the molecules to be separated and the separation resolution required. Thus more rapid separation can be obtained if all the molecules are short or if only approximate sizes (5%–10% accuracy) are required.

It is an advantage of the method and apparatus of the invention that they can provide the superiorities over the conventional electrophoresis systems listed in Table 1.

TABLE 1

Superiority Over Conventional Electrophoretic Systems

| Comparison | This Invention | Conventional Electrophoresis |
|---|---|---|
| Materials | Inexpensive to build and operate; relatively non-toxic separation medium (either aqueous buffer or denaturing organics may be used) | Expensive to operate; separation medium generally uses hazardous polymers and polymerizing agents |
| Set-Up | Easy to load: separation medium may be liquid | Difficult to load: requires mixing, pouring, and polymerizing a gel |
| Loading | Focusing by loading zone electrodes yields a narrow initial sample distribution | Diffusion in loading region can yield a broad initial sample distribution and broad bands |
| Speed | 250 bases/hour/lane for a 0.3 μm feature size (current limit of microfabrication technology) | 100–200 bases/hour on a commercial device |
| Resolution | Bands are reproducible due to a homogeneous separation medium and migration lanes that are physically etched | Bands can lack reproducibility due to inhomogeneities in gel separation medium and curving of separation lanes in gel slab |
| Multiplexing | 100 lanes fit easily on a chip 1 cm square | Multiple lanes in small geometries can be difficult to resolve |
| Safety | Low voltage operation | High voltage operation |
| Clean-Up | Easy to flush device with new separation medium and re-use | Requires disposal of toxic gel and cleaning of supporting plates |

These objects and advantages are achieved by an invention that separates charged particles, in particular charged chemical species, in a separation medium according to differences in the diffusivities of the particles in the medium by use of spatially and temporally variable electric potential. The spatial variations of the electric potential create along the line of separation a plurality of potential wells that attract and trap the charged particles. The potential wells are eccentrically-shaped, with potential minima disposed off-center with respect to the well. In one embodiment, the wells are generally saw-tooth shaped, having one side that is generally steeper than the other side. The potential wells can be disposed in various spatial configurations, with a configuration periodic along the line of separation being preferred. Temporally, the electric potential cycles between at least two states, with two states being preferred. In at least one of the states, the "on-state," the particles are attracted to and trapped in the potential wells. In at least another of the states, the "off-state," the particles are substantially free to diffuse according to their diffusivities in the separation medium. In a preferred embodiment, the on-sate has a duration sufficient to localize each particle in some potential well, and the duration of the off-state is optimized to provide the most rapid separation possible. Thereby, as the potential cycles between the temporal states, the particles diffuse from potential well to potential well in a predictable manner according to the diffusivities and are, thereby, separated according to their diffusivities.

In an important application of the method, the particles are charged biopolymers. In particular, separation of DNA in a medium, such as a liquid, is important, for example, in DNA sequencing and in observing restriction fragment length polymorphism patterns ("RFLP"), genotyping, linkage analysis, microsatellite analysis and other DNA analysis applications. The method is applicable to DNA separation because single-stranded and double-stranded DNA molecules are charged species with liquid-phase diffusivities depending substantially only on their fragment length.

The method and apparatus of this invention are effective with a wide variety of electric fields having spatial variations creating a plurality of potential wells eccentrically placed with respect to their adjacent maximums along the line of separation, and having temporal variations between at least one state trapping the charged particles in the wells and at least one state permitting substantially free diffusion in the medium (which is preferably liquid medium). The potential wells may have a steep and a less steep side, may have an eccentric shape with a narrow minimum for closely confining the trapped particles, or may have a general asymmetric and eccentric shape. The potential wells may be disposed periodically or with varying distance along the line of separation. A preferred potential is of a saw-tooth form along the line of separation. Temporally, the potential may vary between more than two states or may vary continuously. The temporal variation may be constant during a separation or may change during a separation. A preferred potential varies only between an on-state and an off-state.

As the subsequent disclosure makes apparent, the parameters defining the spatial and temporal variation of the electric potential can be selected in view of the diffusivities and charges of the particles to be separated so that the apparatus can be of any physical size. However, in a preferred embodiment, and especially for the separation of DNA fragments, the apparatus is constructed to achieve the fastest possible separation. In such an embodiment, the device is as small as can be constructed using available microfabrication technology.

An embodiment of the separation apparatus comprises a module containing one or more non-communicating separation lanes for holding the separation medium and along which the DNA fragments are separated. The module is constructed from two substrates of centimeter ("cm") scale. One substrate is flat, and the other has channels created by, for example, etching grooves or by depositing walls. When the two substrates are joined, the separation lanes are thereby formed.

Alternate separation lane geometries are possible. One geometry has straight, parallel lanes. A preferred geometry has lanes spaced widely at a loading zone of the module, in order to permit easy physical access to the lanes for loading, but spaced closely at a detection end, in order to permit simultaneous detection of separated fragments in all the separation lanes. Channel sizes can be less than 1 mm, 500 $\mu$m, or 100 $\mu$m, and can be as small as 25 $\mu$m.

The spatially and temporally varying electric potential is created in a preferred embodiment of the separation module by electrodes that are deposited on whichever of the substrates is flat (that does not have grooves). In a preferred embodiment, electrodes lie substantially transverse to said channels and are disposed to create spatially periodic potential wells, each well having a generally eccentric "sawtooth" shape. In this preferred embodiment a voltage difference is applied to the electrodes for an "on" time, $t_{on}$, and the electrodes are at the same potential for an "off" time, $t_{off}$. The potential difference and the "on" time are chosen as sufficient to localize and trap the charged fragments in the potential wells. The "off" time is chosen so that the fragments have a finite probability to diffuse to the next potential well. Cycling the potential causes separation of the charged fragments based on differences in diffusivities. The detailed description (Section 5) makes apparent how to choose the various operational parameters.

The separation medium is chosen to meet several criteria. First, the particles to be separated must be charged in the medium and preferably have a wide range of diffusivities. Second, the medium should both have a high electrical breakdown potential gradient and also not be easily electrolyzed. Preferably, the separation medium is a liquid. Examples of such media appropriate for separating DNA include aqueous liquid media, aqueous buffer solutions, and non-aqueous denaturing liquid media, such as formamide. The invention is not limited to a liquid separation medium. Any media with appropriate electrical properties and in which the particles to be separated are charged and have varying diffusivities can be employed, such as various gels or polymers of various concentrations.

Various enhancements and alternatives in the basic separation module are contemplated by this invention. In an embodiment, liquid separation medium and samples for separation can be loaded through injection ports, which are holes created, for example, by drilling in one of the substrate plates of the separation module. To accommodate such injection ports, the separation lanes may need to be more widely spaced in their vicinity. In addition, an embodiment of the apparatus can include special electrodes to create separate gating potential wells which serve to localize and trap the samples loaded into the loading ports into a compact initial volume prior to separation.

Control of temperature and temperature gradients in the apparatus is desirable and is preferably achieved with a thermal control module in good thermal contact with one or both substrates. An apparatus of the preferred small size provides especially good thermal control, since the small separation medium channels are necessarily in good thermal contact on all sides with both substrate plates. In an embodiment of the apparatus, the thermal control module comprises bi-directional heat transfer devices, such as Peltier thermoelectric modules, arranged for pumping heat in either direction between the separation module and a heat sink which, for example, exchanges heat with an air or water exchange fluid.

In a preferred embodiment, observation of separated particles is accomplished by optical methods. One possible such optical observation method comprises labeling the particles with unique fluorescent tags, generating a fluorescent signal by laser or other excitation transverse to the separation lanes, and detecting the tag fluorescence with standard spectrometers. A transmission imaging spectrograph may be advantageously used to detect fluorescence simultaneously from multiple separation lanes. The invention is particularly adapted to DNA sequence analysis, in which each DNA molecule is labelled with a different one of four spectrally distinctive fluorescent dyes conjugated to one of the four chain terminating ddNTPs. It is also similarly applicable to applications in which particles to be separated are labeled with multiple dyes.

Numerous modifications that could be made to this apparatus by one skilled in the relevant art are contemplated by this invention. Some of these modifications include the following. The temperature of the media can be varied to enhance diffusivity. Separation media such as polymer solutions or gels can also be used. A variety of materials can be used as the substrate of the separation module and the electrical components, such as the insulators, conductors, and resistors, of the apparatus. Different electrode geometries could be used to obtain electric potentials that function to create potential wells. For example, electrodes may be deposited as a layer contacting the bottom of the separation lane; they may be thicker, extending across the thickness of the separation lane; or they may have an intermediate thickness. Alternately, the potential wells can be created by electrodes external to the separation lanes. A variety of lane geometries are possible, including linear, piece-wise linear, open curvilinear, or closed curvilinear geometries. In a circular geometry, the lanes run around the circumference of a cylinder.

The method and apparatus of this invention has utility in many areas. Biological research laboratories need easy-to-use systems for high-throughput, multiplexed DNA analysis for genome sequencing. Medical laboratories also have growing needs for rapid, low-cost DNA analysis and sequencing. Separation of other charged particles, for example RNA and proteins, has similar uses in research and diagnostic laboratories.

4. BRIEF DESCRIPTIONS OF THE DRAWINGS

These and other objects, features, and advantages of the invention will become apparent to those of skill in the art in view of the accompanying drawings, detailed description, and appended claims, where:

5. DETAILED DESCRIPTION OF THE INVENTION

Sec. 5.1 describes the structure of an exemplary separation device according to this invention. Sec. 5.2 describes in a summary fashion the operation of a separation method and device. Sec. 5.3 describes in more detail the operation of the separation method and device, and provides a method for the selection of method operating conditions and device design parameters. Sec. 5.4 describes the important case of the separation of DNA. Finally, Sec. 5.5 describes exemplary methods for microfabricating a separation device according to this invention.

5.1. Description of A Separation Device

Figure 1:
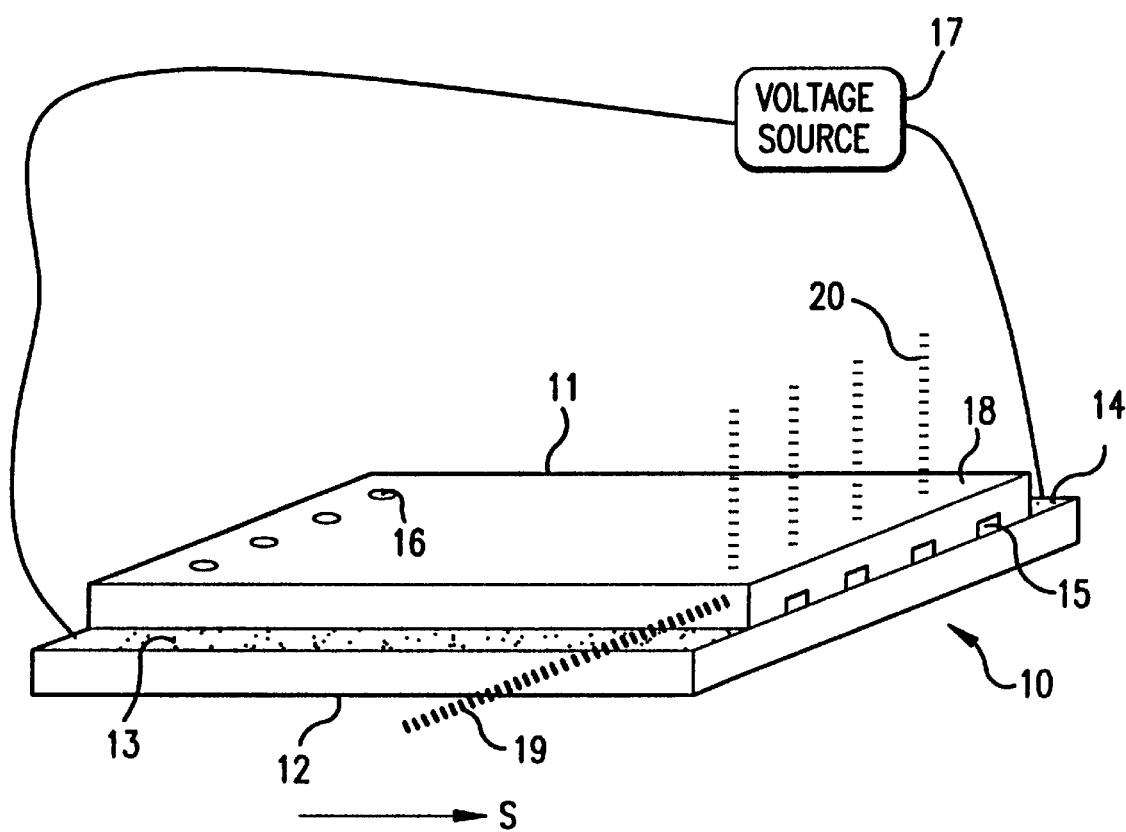
FIG. 1 illustrates a separation device according to the present invention.

FIG. 1 illustrates a separation device according to this invention. This separation device and its particular embodiments, device types I and II, are the preferred physical structures for the device. However, charged particle separation according to the method of this invention can be practiced in any other physical structure having one or more separation lanes that hold a separation medium and that are subject to electric potentials according to the method of the invention. For example, it can be practiced in one or more tubes, perhaps of capillary size, with externally imposed electric potentials. Alternatively, the invention can be practiced in an conventional configuration with the separation medium disposed as a slab with the separation lanes running in the slab.

In FIG. 1, separation device 10 includes two substrates, upper substrate 11 and lower substrate 12, which define between them one or more separation lanes, such as lane 15. Lane 15 extends between loading port 16, which, for example, could be a hole drilled in upper substrate 11, and an observation zone indicated generally at 18. In the case where the charged particles are fluorescently tagged, observation can be conveniently effected by illumination of the observation zone 18 by laser beam 19. Fluorescence 20 induced in particles in the separation lanes is observed by a spectrometer. Standard optics together with a CCD detector can detect 0.01 femtomole ("fm") of fluorescent dye-labeled particles in an illuminated area 100 $\mu$m on a side. See, e.g., J. W. Simpson et al., "Apparatus and method for the generation, separation, detection and recognition of biopolymer fragments," U.S. patent application Ser. No. 08/438,231 filed May 9, 1995, which is herein incorporated by reference in its entirety.

The electric potential according to a method of this invention is generated along channel 15 by a pattern of electrodes, to be described hereinbelow, deposited or affixed to one or both substrates. Each electrode is connected to one of electrode pads 13 or 14, through which it is energized by a time varying voltage conducted from external voltage source 17.

Operational parameters of the method can be selected so that the device may be constructed to be of any size. For faster charged particle separation, it is preferable to make the device as small as possible within the constraints of a chosen fabrication or micro-fabrication technology. Small size also permits placing an array of channels on single substrates and thereby achieving multiple simultaneous separations. However, the device should be sufficiently large both so that the charged particles to be separated move independently of each other during separation and also so that at least several hundred particles can be transported through the device together. In the case where the charged particles are charged molecules, this latter condition is easily satisfied by making the smallest dimensions in the device larger than 50 to 500 times the molecular dimensions.

Many materials can be used for substrates, channel walls (in type II devices), and electrodes. One limitation is that any material exposed to a separation lane should be substantially inert to contents of the lane, such as the separation medium used and charged particles to be separated. Either the materials should be inherently inert or should be protected through a passivation layer, for example a silicon oxide layer deposited over electrodes. Further, for ease of detecting the separated particles, it is preferable that the substrate permit the use of fluorescent labels. Thus the substrate should be substantially transparent to light at the excitation and induced fluorescence wavelengths. Amorphous silicon oxide is an example of an acceptable substrate for most fluorescent dyes, such as those conventionally used to label DNA fragments. More examples of acceptable materials are found in Sec 5.5.

The charged particles to be separated can range from individual molecules of all sizes, to complexes of any number and kind of molecules, and to particles of macroscopic dimensions.

The separation lanes are filled with a separation medium that preferably displays certain properties. A first property is that it dissolves and ionizes the particles to be separated. A second property is that the types of charged particles to be separated have different diffusivities in the medium; the greater the diffusivities overall and the greater the diffusivity difference the more preferable the medium. A third property for rapid separation is that the medium withstands large potential gradients. Therefore, the medium is preferably resistent to electrolysis at the potentials imposed, and the higher the breakdown electric field the better. Finally, it is preferable that the medium have a small dielectric constant and a small ionic strength since the strength of an electric field is reduced by the dielectric shielding due to the medium and by ionic shielding due to contained ions. This latter property is, of course, constrained by the necessity to solvate charged molecules, which generally requires a high dielectric solvent and a finite ionic strength due to the presence of counterions.

Separation mediums meeting these conditions for a particular type of charged particle to be separated can be most readily determined by experimentation. For separating biopolymers, such as DNA, suitable separation media are the aqueous solvent or aqueous buffers commonly used in conventional electrophoresis. Alternatively, the medium may also be a denaturing solvent like formamide. Other organic solvents that can solvate molecules in a charged state and permit sufficient potential gradients, for instance DMSO (dimethyl sulfoxide) or alcohol solutions, are also useable. Further, dilute gels or polymer solutions are also possible separation mediums.

The separation device may be operated at any temperature compatible with its construction materials and with the separation medium used. All examples and calculations herein assume operation at ambient temperature, approximately 298 K., unless otherwise stated. Regardless of the operational temperature, it is important that thermal gradients be minimized to keep the separation medium substantially uniform throughout each separation lane. This can be achieved by placing the top or bottom substrate, or both, of the separation device in thermal contact with heat sinks or sources, as appropriate.

Two particular embodiments of the separation device illustrated in FIG. 1, called types I and II, are further described in the subsections which follow. In device type I, channels forming the separation lanes, such as channel 15, are etched on one side of one of the substrates 11 or 12. In device type II, the preferred embodiment, separation channels are formed on one of the substrates by depositing parallel channel walls. In both embodiments, electrodes are deposited on one of the substrates.

5.1.1. Device Type I

Figure 2:
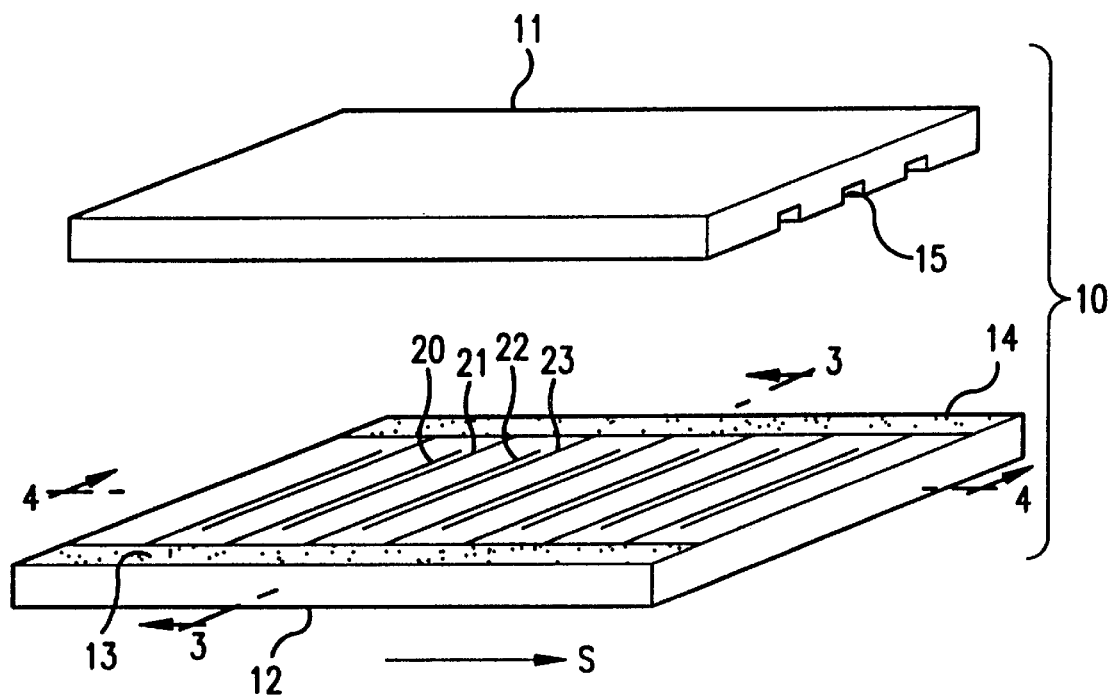
FIG. 2 illustrates an exploded view of an embodiment of type I of the separation device of FIG. 1.

FIG. 2 is an exploded view of an exemplary embodiment of device type I. Device 10 includes top substrate 11 and bottom substrate 12. One or more separation channels 15 are fabricated in top substrate 11, for example, by etching or micro-machining. Separation occurs along the channels, which, therefore, define separation direction S. The geometry of a channel is preferably approximately semicircular to rectangular with a width of approximately 50 $\mu$m and a height of 10 $\mu$m. Smaller heights and widths are preferable because less sample is required for analysis. The width may range to a large distance, comparable to the widths of traditional gel-based electrophoresis devices. The height is preferably sufficiently small that the electric potentials generated are sufficient to localize the particles during the on-condition, a condition most readily determined by experimentation for a given device geometry using particles representative of those to be separated. Each channel extends for substantially the entire length of the substrates, which is typically from 1 to 10 cm, but is chosen according to the design methods of Sec. 5.3. and 5.4. The channels are spaced apart as closely as possible, and are preferably spaced apart no less than a distance approximately equal to their width. Top plate 11 may be fabricated with drilled loading port 16 in FIG. 1, as further described below. The diameter of such a port is selected to permit loading into the lanes of the particles to be separated. The channels may be substantially parallel or, alternately, may converge from a wide spacing in the vicinity of the loading port to a narrow spacing in the observation zone. The two substrates are fused together so that the channels fabricated in the top plate are sealed to create closed particle separation lanes. The top substrate has recessions with respect to the bottom substrate to allow the electrode pads to be exposed in order to make electrical connection to external voltage source 17.

Two pluralities of interdigitated electrodes situated facing each other and connected electrode pads 13 and 14, each plurality of electrodes connected to one of the two electrode pads, are deposited on the flat upper surface of bottom substrate 12. Alternatively, electrodes can be deposited on the non-flat surfaces of upper substrate 11. Electrodes 20 and 22 are exemplary of that plurality of electrodes connected to pad 13, and electrodes 21 and 23 are exemplary of that plurality connected to pad 14. These electrodes preferably extend substantially transverse to separation axis S. Less preferably, the electrodes are inclined with respect to the separation axis and separation lanes, as would be the configuration with converging separation lanes. The greater the angle of inclination, the less efficient and the lower the resolution of the particle separation. The thickness of each of these electrodes is preferably less than approximately 0.1–0.2 μm, and less preferably less than 1 μm, although large sizes will not necessarily interfere with the operation of the device. The width of each of these electrodes, their feature size denoted R', is preferably less than approximately 1–2 μm. Larger values for R' will not interfere with the operation of the device, but will result in less preferable operation times scaling as $R'^2$. Feature sizes of approximately 1 μm are readily achievable with standard microfabrication techniques. Preferably, each plurality of electrodes attached to electrode pads 13 and 14 are periodically positioned with a uniform separation of L. For example, electrodes 20 and 22 are separated by distance L, as are electrodes 21 and 23. Preferably, each plurality of electrodes is displaced with respect to one another by a displacement of R. For example, the centers of electrodes 20 and 21 are separated by distance R, as are the centers of electrodes 22 and 23. Preferably R is approximately equal to R', while L is chosen so that R/L is less than approximately 0.1, although ratios up to 0.5 may be employed. Methods for optimally choosing R, L, and R/L, in terms of feature size R', achievable in a selected fabrication technology, are described in Sec. 6.2. Alternatively, R, L or R/L can be systematically varied along a separation axis to optimize certain aspects of partial separation according to the model described in Sec. 5.2 and 5.3.

Figure 3:
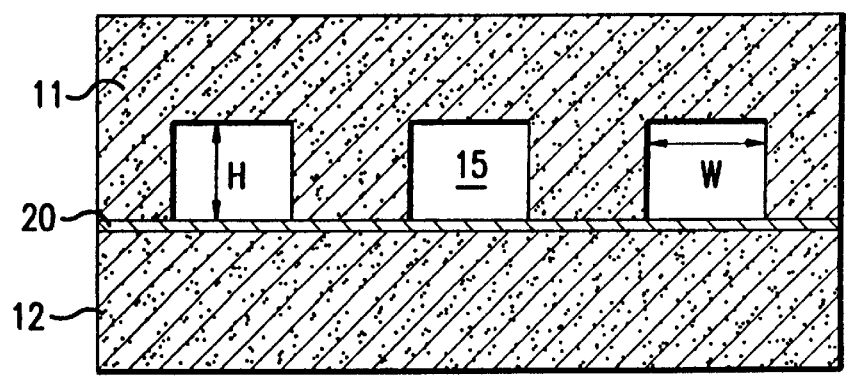
FIG. 3 illustrates a cross sectional view transverse to the direction of separation of the device of FIG. 2.

FIG. 3 illustrates a cross sectional view of device 10 along axis 3—3, which is transverse to separation direction S. Top substrate 11 and bottom substrate 12 form three channels, such as channel 15, which are sealed to form separation lanes. Exemplary electrode 20 extends along the bottom of the channels, preferably covered with a passivation layer, if needed.

Figure 4A:
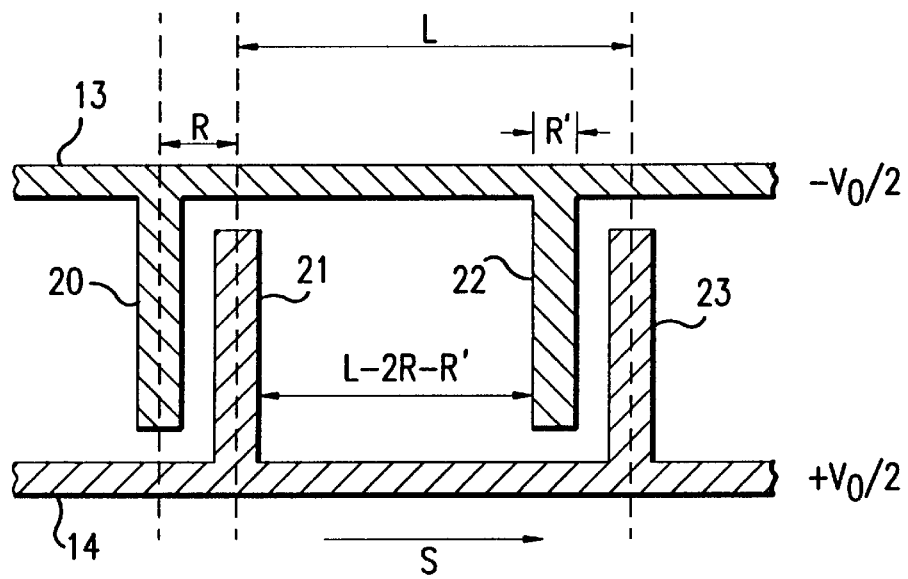
FIGS. 4A–4B illustrates in detail the electrodes of the device of FIG. 2 and the electric potential generated by the electrodes.

FIG. 4A schematically illustrates the two pluralities of the electrodes in more detail. Electrodes 20 and 22 of one plurality of electrodes are attached to electrode pad 13, while electrodes 21 and 23 of the other plurality are attached to pad 14. Electrodes of one plurality are separated by distance L. The centers of neighboring electrodes, one of each plurality, are separated by distance R. Each electrode has width R'. Therefore the adjacent edges of electrodes 21 and 22 are separated by distance L-2R-R', and the adjacent edges of electrodes 20 and 21 (or 22 and 23) are separated by R-R'. Pads 13 and 14 are charged to potential $-V_o/2$ and $+V_o/2$, respectively. When $V_o>0$, the direction of separation of positively charged particles is S. When $V_o<0$, S is the direction of separation of negatively charged particles.

Figure 4B:
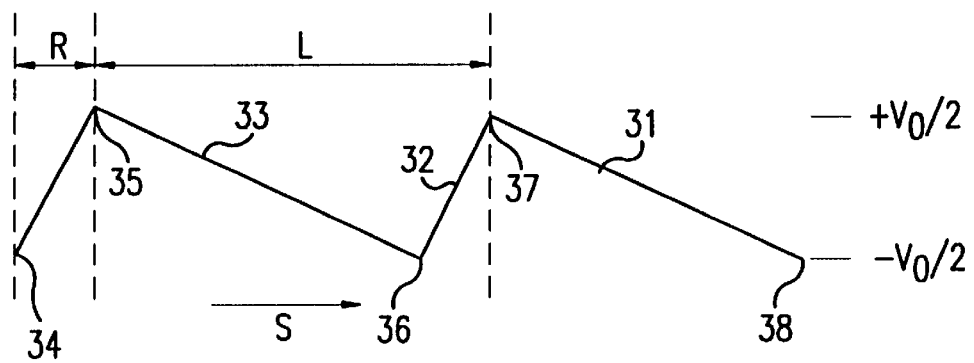

FIG. 4B illustrates the approximate, idealized electric potential generated by the two pluralities of electrodes as observed along a separation lane. The potential consists of a series of potential wells, varying from a minimum of $-V_o/2$ in the vicinity of the electrodes attached to pad 13 to a maximum of $+V_o/2$ in the vicinity of the electrodes attached to pad 14. The potential is generally of a saw-tooth shape, periodic in space, with each period or potential well having a uniformly and eccentrically placed minimum. Each period has a relatively shorter and more steeply rising portion 32, between positions 36 and 37 separated by distance R, and a relatively longer and move slowly falling portion between positions 35 and 36 separated by distance L-R. The direction of separation, arrow S, is the direction from one minimum to its nearest adjacent maximum. Thus, arrow S is in the direction from minimum 36 towards its nearest adjacent maximum 37. The potential wells are uniform in that these directions for all the wells are all aligned in the same direction, here arrow S. Further, it is clear that the potential wells remain stationary in space in the vicinity of the generating electrodes. In case the pads are charged to opposite potentials, the rising and falling portions are interchanged.

The minimum size for each potential well is generally limited by the preferred aspect that it contain at least several hundred of the particles to be separated. The well should also be large enough to allow the contained particles to move independently without any correlations. In the preferred application in which charged biopolymers are to be separated, this is satisfied if R is larger than approximately 0.1 μm.

Figure 5:
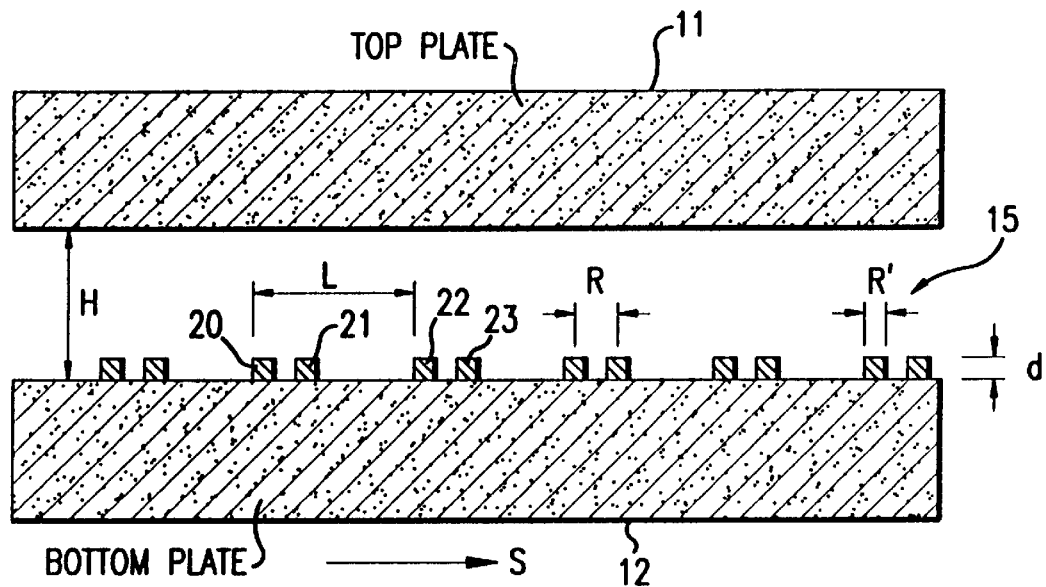
FIG. 5 illustrates a cross sectional view along the direction of separation of the device of FIG. 2.

FIG. 5 illustrates a cross sectional view of device 10 along axis 4—4 of FIG. 2, the direction of separation, in a separation lane, such as lane 15. The separation lane is bounded above by top substrate 11 and below by bottom substrate 12, which are separated by H, the lane height. The lane height is preferably chosen to be 10 μm, with larger heights possible subject to the constraint that the electric potential be sufficiently strong to localize the particles during the on-condition. Electrodes, generally at 20, 21, 22, and 23, on bottom plate 12, are substantially transverse to the separation direction S, and are exposed in the separation lane to generate the potential. These electrodes are of height d, preferably less than approximately 0.1–0.2 μm, of width R', preferably from 1–2 μm, and of separation R, preferably approximately 2R', with smaller distances more preferable since they afford more rapid separations. The electrodes are preferably periodically placed with a periodicity distance L, preferably chosen so that R/L is 0.1 or less. Alternatively, R/L is less preferably less than 0.3; the device continues to function, albeit less efficiently, up to a limiting ratio of 0.5 (i.e. symmetric wells).

The device can be advantageously adapted to have a loading zone for easy loading of particles prior to separation. To allow easy loading with current loading technologies, the loading ports preferably have a diameter of the order of 50–100 μm, the size of micropipettes. Correspondingly, this is a convenient scale for the width and separation of the separation lanes. Alternatively, narrower separation lanes can be a widely spaced in a loading zone to accept ports of the preferable size and can converge to a narrower spacing in an observation zone. To achieve optimum separation resolution and speed, it is preferable that all the particles are attracted into a single potential well prior to separation and that the spacings between sequential potential wells be as previously described.

Figure 6:
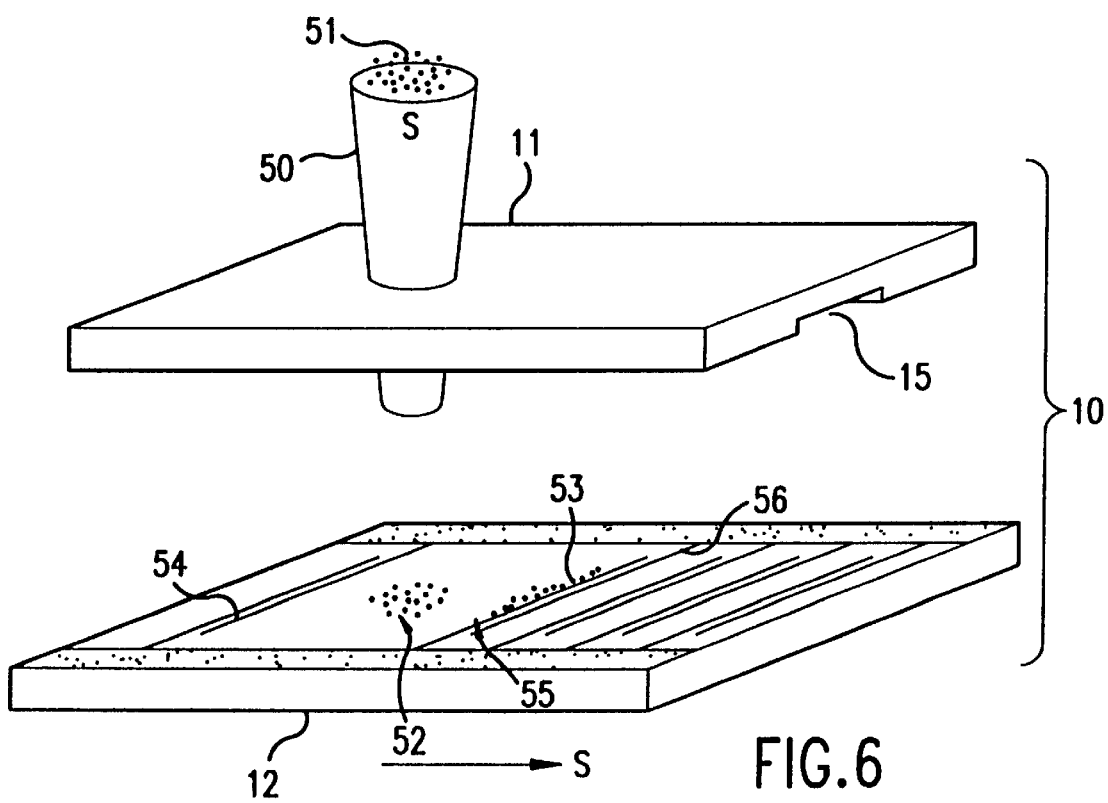
FIG. 6 illustrates the loading zone of the device of FIG. 2.

FIG. 6, an expanded and exploded view of device 10 about loading port 16 of FIG. 1, illustrates a loading zone adapted to meet these properties. Particles to be separated are introduced from outside the device, at position 51, through pipette 50, or similar mechanism, to the interior of separation lane 15, at position 52. Electrodes 54 and 55 underneath port 16 have an increased separation of the order of the diameter of port 16. During or after particle loading, a potential is applied to the electrode pads, and thus to electrodes 54 and 55, for a time sufficient to attract all the particles into the close vicinity of electrode 55, at position 53. A sufficient time can be estimated in a manner similar to the determination of $t_{on}$ described in Sec 5.3. After the particles have been attracted and trapped, particle separation can begin. Alternative electrode configurations may be used in the loading region to achieve a smaller initial distribution of particles to be separated. For example, electrode 56 may be separately held at a potential more attractive than that of electrode 55 to localize all particles between these electrodes prior to beginning separation.

5.1.2. Device Type II

Figure 7:
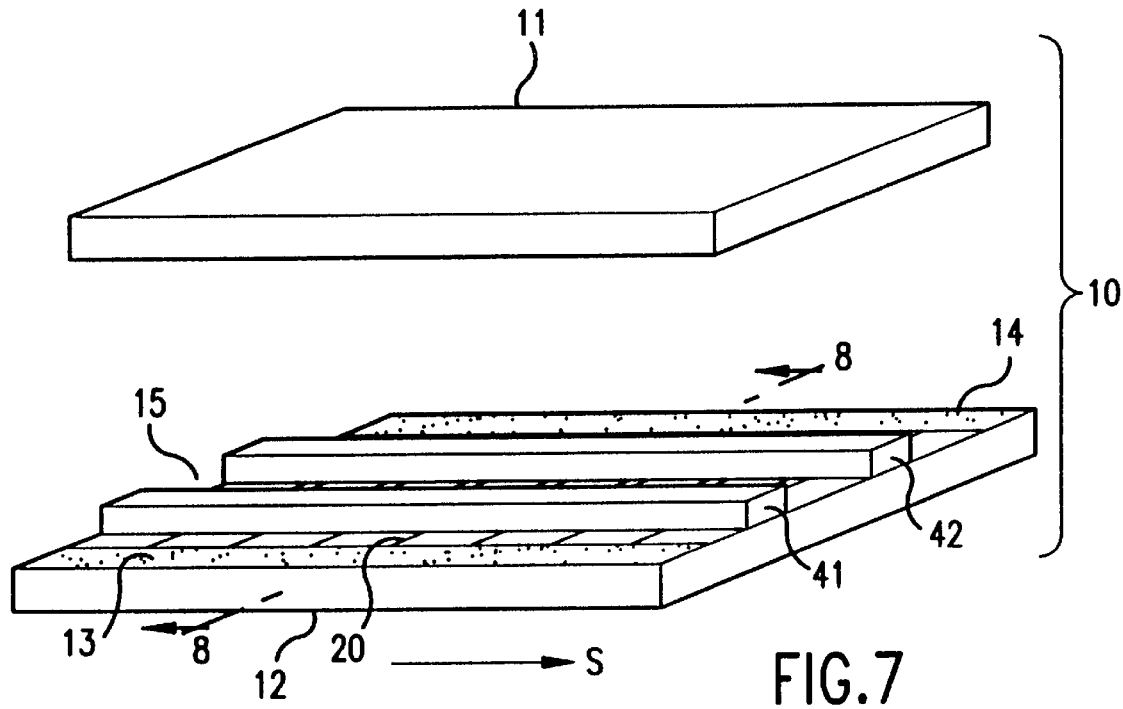
FIG. 7 illustrates an exploded view of an embodiment of type II of the separation device of FIG. 1.

FIG. 7 is an exploded view of an exemplary embodiment of device type II, the preferred embodiment of the separation device. Device 10 includes top substrate 11 and bottom substrate 12. A pattern of electrodes and connected electrode pads similar to that of device type I is deposited on the flat upper surface of bottom substrate 12. Alternatively, electrodes can be deposited on the non-flat surfaces after the channel walls have been fabricated or on the bottom surface of upper substrate 11.

The only difference between the two device types is that in device type II separation lanes are formed by fabricating substantially straight channel walls along direction of separation S on one of the two substrates. FIG. 7 illustrates channel walls 41 and 42 forming separation lane 15 fabricated on the upper surface of the bottom substrate, on top of the electrode pattern previously fabricated. As in device type I, the separation lanes are exposed to the electrodes, which run preferably substantially transverse to the direction of separation S and less preferably have an angle of inclination less than 48°. The geometry of the separation lanes is substantially rectangular with dimensions similar to the lane dimensions of device type I.

The top and bottom substrates are fused together so that the channels walls together with the top and bottom substrates form sealed and closed separation lanes. The top substrate has offsets with respect to the bottom substrate to allow the pads to be exposed in order to make an electrical connection with voltage source 17.

Figure 8:
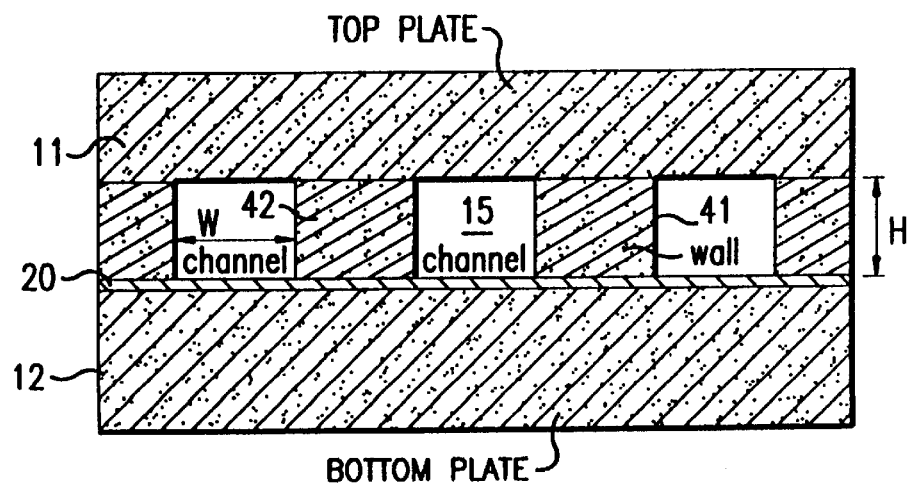
FIG. 8 illustrates a cross sectional view transverse to the direction of separation of the device of FIG. 7.

FIG. 8 illustrates a cross sectional view of device 10 along axis 8—8 in FIG. 7, which is transverse to separation direction S. Top substrate 11 and bottom substrate 12 bound three channels. Channel 15 is bounded by wall 41 and 42 fabricated on the surface of one of the substrates. Exemplary electrode 20 extends along the bottom of the channels.

5.2. Summary Operation of Method

A method of this invention, which is implemented in the devices described in Sec. 5.1, is illustrated in FIGS. 9A–E. These figures illustrate the separation of two types of charged particles, a larger particle type indicated by larger rods, as at 91, and a smaller particle type indicated by smaller rods, as at 92. The electric potential is depicted by curves 90. It assumes a saw-tooth shape for a time $t_{on}$ in FIGS. 9A, 9C, and 9E, and is flat for a time $t_{off}$ in FIGS. 9B and 9D. In the case where these particles are single-strand DNA molecules of various sizes, the molecules are in reality more likely to be globular in shape.

Figure 9A:
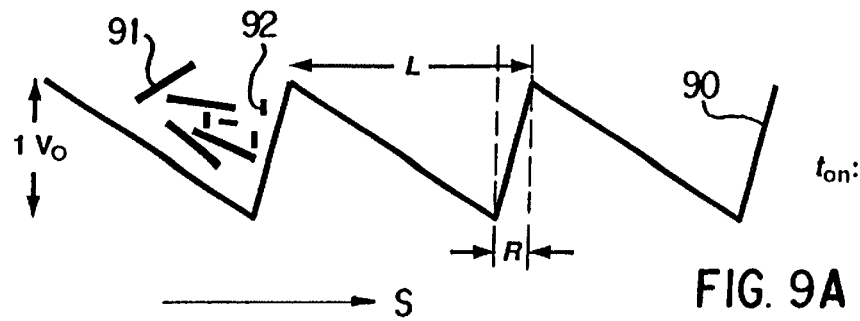
FIGS. 9A–9E illustrate in summary form the operation of a method of the present invention.
Figure 9B:
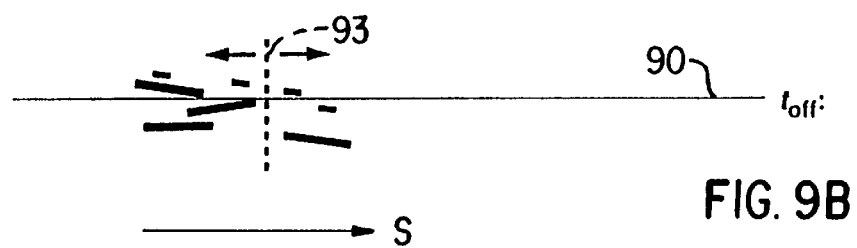
Figure 9C:
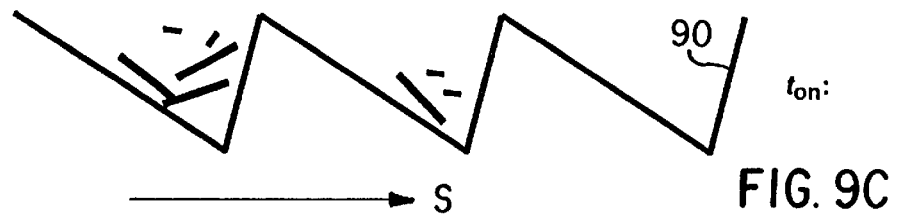
Figure 9D:
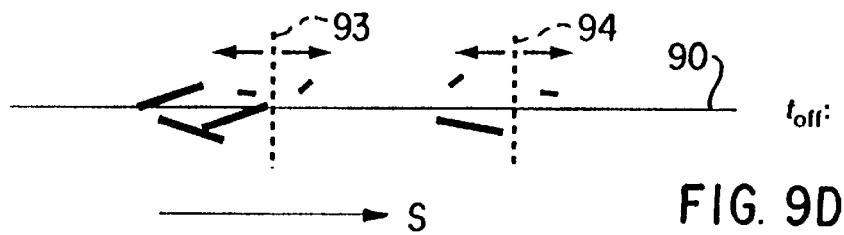
Figure 9E:
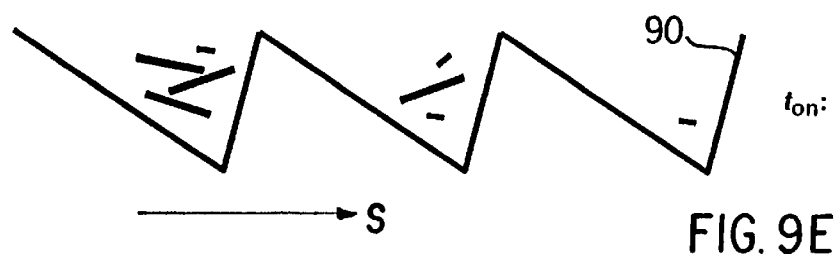

FIG. 9A represents the beginning of a separation at which time all the particles are trapped in the left-most potential well. In FIG. 9B, the potential is flat for $t_{off}$, during which time the particles diffuse equally in both directions along the separation channel. The diffusion is indicated generally at 93. In FIG. 9C, the potential again assumes a saw-tooth shape, and particles that have drifted to the right at least a distance R to the next potential well are attracted to and trapped in the middle well. However, particles that have diffused less than a distance R are attracted to and trapped in the original left-most potential well. Since smaller particles with larger diffusion constants are more likely to diffuse further than larger particles with smaller diffusion constants, two of the small particles but only one of the large particles arrive in the middle potential well. In FIG. 9D, the potential is again flat and the particles diffuse equally in both directions from both potential wells at 93 and 94. Finally, in FIG. 9E, when the potential again assumes a saw-tooth shape, one of the small particles has diffused from the middle well far enough to be attracted to and trapped in the right-most well, and two small particles are in the middle well. On the other hand, nd large particles have diffused far enough to be in the right-most well, and only one large particle is in the middle well. It can be seen, therefore, that the particles with the higher diffusion constants will be selectively transported to the right through the device.

The differential forward motion of the particles is due to their diffusion. The potential wells remain spatially stationary, and when on, only serve to attract particles into their minimum. If the distance R is too great for significant diffusion during the time the potential is off, the particles remain stationary in the device.

In particular, this method can separate DNA molecules because the diffusion constant, D, of DNA depends predictably on the molecular dimensions, and thus on the number of bases, N, in single-stranded or double-stranded fragments (Doi et al., 1986, *The Theory of Polymer Dynamics*, Clarendon Press, Oxford, p. 300). Experimental measurements of dsDNA and theoretical prediction for ssDNA show that for aqueous solutions:

$$D_{dsDNA} \approx 1.14 \times 10^{-6} N^{-1} \text{ cm}^2/s$$
$$D_{ssDNA} \approx 1.14 \times 10^{-6} N^{-0.59} \text{ cm}^2/s \qquad (1)$$

See, e.g., Weast, ed., 1987, *Handbook of Chemistry and Physics*, Chemical Rubber Publishing Co., Boca Raton, Fla., and Sec. 5.4.

We now consider several of the operating conditions for the device. The separation speed of a potential depends on the its eccentricity, the more eccentric the faster the separation. Eccentricity refers to the location of the potential minimum with respect to the potential well, the closer the potential minimum is to the nearest adjacent maximum the more eccentric is the potential. For example, for a series of saw-tooth potentials with the same period, L, the potential with the smallest R/L ratio operates fastest. Of course, R cannot be substantially smaller than the feature size, R', available in the chosen fabrication technology, and cannot be so small that the resulting potential gradient exceeds the breakdown field of the separation medium. Also, L is preferably large enough that the potential well can trap at least several hundred independently moving particles.

The voltage, V, applied across the electrode pads should preferably be sufficiently large that $t_{on}$ is as small as reasonably possible compared to $t_{off}$. However, it should not be so large that substantial electrolysis occurs at the electrodes, that the breakdown field of the separation medium is exceeded, or that resistive heating of the separation medium interferes with separation resolution.

In Sec. 5.3, methods are provided for selecting R, L, R/L, $t_{on}$, $t_{off}$, and V based on a model of the separation method in a narrow channel with substantially transverse electrodes. Operating parameters for an actual device should be correctly predicted to within an order of magnitude by this model. If needed, precise operating parameters can be determined from the predicted parameters by routine experimental optimization. For example, in the case of separation of DNA molecules, operation of the device with a DNA standard containing a ladder of fragments of known lengths can be used to optimize the predicted operating parameters.

The method of this invention is adaptable to charged particles of all sizes. The charged particles to be separated can range from individual molecules of all sizes, to complexes of any number and kind of molecules, and to particles of macroscopic dimensions.

5.3 Detailed Operation A Method

INTRODUCTION

In this section, the operation of a method of this invention is described in more detail. This description makes use of the following variables:

| | |
|---|---|
| L | the spatial period of the electric potential; |
| R | the distance from a potential minimum to the nearest potential maximum (the extent to which R is less than L/2 is a measure of the eccentricity of each period of the potential); |
| P | the temporal period of the electric potential (P = $t_{on} + t_{off}$); |
| f | the temporal frequency of the electric potential (f = 1/P); |
| $t_{on}$ | the time when the potential is applied, during which the particles are attracted and trapped in the potential wells; |
| $t_{off}$ | the time when the potential is not applied, during which the particles can freely diffuse; |
| Q | the charge of a charged particle; |
| $V_o$ | the applied potential difference; |
| T | the temperature; |
| D | the diffusion constant of one type of charged particle to be separated; and |
| D + ΔD | the diffusion constant of another type of charged particle to be separated (with ΔD referring to the difference in diffusion constants); |
| $N_{cyc}$ | the number of temporal cycles of the potential for a complete separation run; |
| $T_{tot}$ | the total time of a complete separation run ($T_{tot}$ = P*$N_{cyc}$ and $N_{cyc}$ = f*$T_{tot}$); |
| $V_{drift}$ | the drift velocity of charged particles in the electric potential; and |
| $L_{tot}$ | the total length of the separation lane. |

First, the preferred embodiment for the method and device of this invention is presented. Second, a method is presented for selecting operational and device parameters in an optimal manner. Third, exemplary alternative operation modes within the scope of this invention are described.

5.3.1. An Embodiment Of The Invention

The section includes a discussion of the spatially and temporally varying potential of a method of this invention, of criteria for the operational method parameters, and of a preferred model of the method in view of these criteria. Initially, it is assumed that ΔD<<D; subsequently, the case where ΔD≧D is described.

THE POTENTIAL

Figure 10:
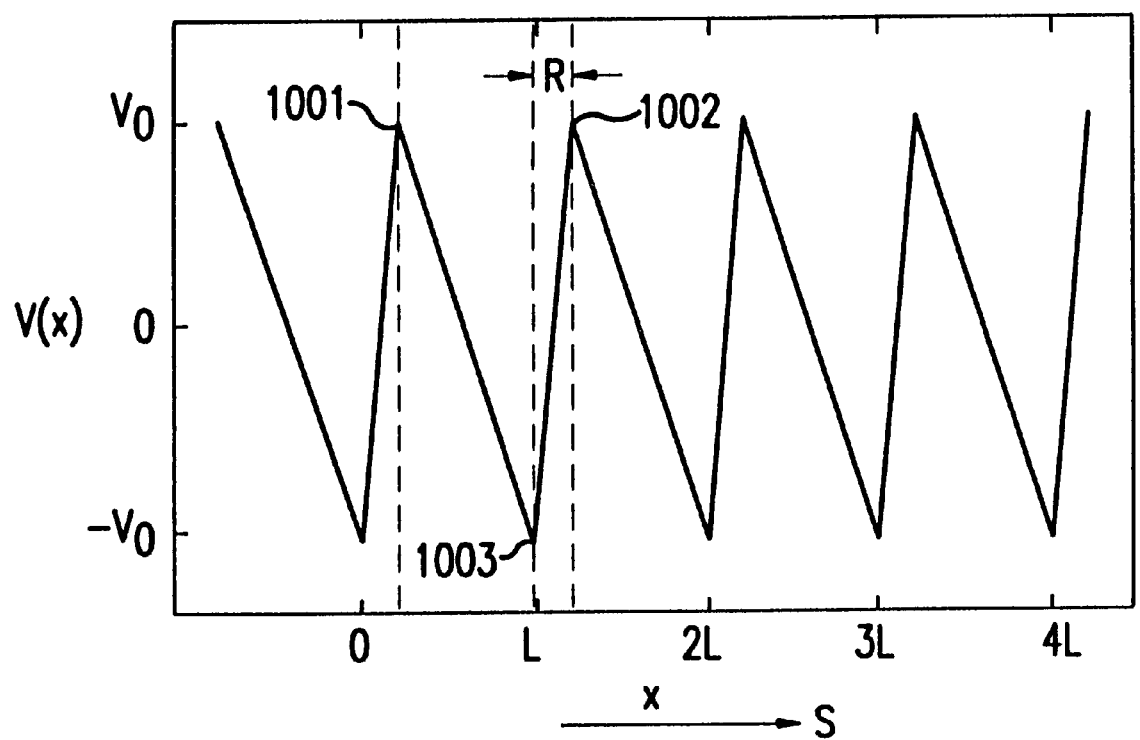
FIG. 10 illustrates a form of electric potential adaptable for use in the method of FIGS. 9A–9E.

FIG. 10 illustrates generally and schematically an electric potential, V(x), as a function of distance along the separation axis, x, that is usable in this invention. This potential is spatially periodic with spatial period L. Alternatively, non-spatially periodic potentials can be used in this invention. Every period of the potential should be eccentric with each minimum of the potential closer to the adjacent maximum in one direction along the separation lane. This direction is the direction of particle separation S. The separation between a minimum and its closest adjacent maximum is expressed by R, with R<L/2. For example, minimum 1003 is spaced a distance R, which is less than L/2, from adjacent maximum 1002, but is spaced a distance L–R, which is greater than L/2, from adjacent maximum 1001. All the minimums are closer to the maximum adjacent in the direction S. This potential closely approximates the potential generated near the electrode pattern of device types I and II.

When $V_o$>0, the potential of FIGS. 11A–D separates positively charged particles in the direction S. In this case, negatively charged particles are transported through the device in the opposite direction, but are not necessarily separated. To separate negatively charged particles along direction S the polarity of the potential must be reversed, that is $V_0$<0. In this latter case, positively charged particles are transported through the device in the opposite direction, but not necessarily separated. Advantageously, particles can be loaded in a loading zone at one end of the device and the device operated first with one polarity and second with the reverse polarity to sequentially separate particles of both charges. In the preferred embodiment specific to separations of DNA, however, it is envisioned that all the particles have a negative charge.

The exact spatial configuration, V(x), of the potential is not important to the operation of this invention. What is important is, first, that the potential consist of alternating potential maximums and potential minimums along the axis of separation. The wells are generally separated by distance L. Second, all the maximums and all the minimums should be eccentrically placed in that each minimum should be closer to its adjacent maximum in the direction of separation than it is to its adjacent maximum in the direction opposite to the direction of separation. The distance between a minimum and the nearest maximum is generally R. Distances L and R are conveniently taken to characterize a region of the potential. The method of this invention is adaptable to any potential meeting this constraint and separates particles in a direction of separation of a charge which is attracted into the wells. It is preferable that the potential be periodic having similar potential wells, and all subsequent discussion assumes spatial periodicity. Spatial periodicity is not required by the invention, however.

For greatest separation efficiency, that is for minimum separation time, it is preferable that the potential is homogeneous in directions transverse to the migration axis. The method and device of this invention functions, albeit at reduced efficiency, if the electric field vectors have components perpendicular to the axis of separation or, in other words, perpendicular to a disposition longitudinal to the direction of separation. The efficiency of the operation of the method is approximately cos(θ), where θ is the angle of the electric field vectors relative to a disposition longitudinal to the direction of separation. Thus it can be appreciated that the method functions for nearly all relative directions between the electric field and the direction of separation. However, it is preferable that all electric field vectors be substantially longitudinal to the axis of separation. In this context, substantially longitudinal is preferably taken to means that θ is less than about 45°–50° so that cos(θ) is therefore greater than about 0.5.

Moreover, in certain embodiments of the invention, it is possible to adjust operational parameters to minimize the effect of transverse inhomogeneities in the potential. For example, in an embodiment in which the electric potential is generated by electrodes adjacent to the separation lanes and in which the potential varies from a substantially off-state for a time $t_{off}$ to a substantially on-state for a time $t_{on}$, for instance, in device type I or II, the potential may be inhomogeneous transverse to the migration axis due to electrode size and spacing in comparison to preferable separation lane widths. Since the electric potential decays away from electrodes, the potential wells are deepest closest to the electrodes. If the lane width is greater than the smallest inter-electrode spacing and if the electrodes do not entirely surround the channel, the potential well may be weak at the side of the lane furthest from the electrodes. However, this does not present a problem to this invention, because, first, $t_{on}$ is optimally selected to attract and trap the charged particle at the electrodes and, second, $t_{off}$ is optimally selected so that the particles diffuse at most a distance approximately equal to the inter-electrode spacing. Thus, since the particles to be separated remain in a region of relatively strong potential wells throughout the optimal operation of the device, potential inhomogeneity above the electrodes can be substantially neglected. Also, the electric potential may be perturbed near the separation lane walls. Again, this inhomogeneity can be substantially neglected because during operation because the charged particles remain where the potential wells are relatively strong.

The electric potential also varies temporarily. All that is required is that the potential vary from a first strength, in which the particles are attracted to and trapped in the spatial potential wells, to a second strength, in which the particles are relatively free to diffuse in both directions, having a non-zero probability of diffusing into the nearest potential well. This probability can be quite small, 0.1% or less, or quite large, nearly 100%. It is preferably optimized to obtain the fastest possible separation. For convenience only and not by way of limitation, subsequent description assumes that the temporal variation is periodic, with a period P and a frequency f, varying between an on-state and an off-state. For a time $t_{on}$, a potential $\pm V_0/2$ is applied, and for a time $t_{off}$, no potential is applied. Thus, during each cycle of operation of time T, the potential is on for time $t_{on}$ and off for time $t_{off}$, with $t_{on}+t_{off}=T$ and $f=1/T$.

Although, the method is modeled with a temporally periodic two state potential, potentials with other temporal variations can be used in the invention. First, the temporal variation need not be periodic. For example, the temporal period may change systematically as a separation progresses. Second, it is possible to include other states in the cycling. For example, a state can be included to focus the particles more tightly at the bottom of a well at the start of each cycle so as to obtain a smaller value for the parameter R. The potential may also vary continuously in time.

PREFERRED CONSTRAINTS ON METHOD PARAMETERS

When the potential is on, the potential wells should be sufficiently deep to attract and trap against thermal agitation the charged particles to be separated. This condition is met if $V_o$ is sufficiently large so that the following inequality is valid.

$$\frac{\phi V_o Q}{k_b T} \gg 1 \quad (2)$$

($k_b$ is Boltzman's constant.)

When the potential is off, particles of diffusion constant D in one well should have a finite probability, $\alpha_D$, of diffusing a distance R in the direction of separation to the next potential well. The probability is advantageously chosen by optimizing $t_{off}$ to obtain the fastest possible separation. In the preferred model for this invention, this condition is expressed as a relation between R and $t_{off}$ given by $$\alpha_D = 1/2 \, erfc\left(\frac{R}{\sqrt{4Dt_{off}}}\right) \quad (3)$$

"erfc" is the complementary error function.

Further, when the potential is off, particles of diffusion constant D should have a probability of diffusing backward a distance L−R to the previous potential well that is preferably less than $\alpha_D/100$. In the preferred model for this invention, this results in the condition between R, L, and $\alpha_D$.

$$\sqrt{4Dt_{off}} \leq R \ll L \quad (4)$$

The probability that particles diffuse a distance L+R to the potential well beyond the next closest adjacent well is necessarily smaller than the probability they diffuse backward a distance L−R.

These conditions are easily met. For example, if $\alpha_D=0.05$ and R/L=0.1, then the probability of backward diffusion is vanishingly small, about $10^{-50}$, and the probability of diffusing by more than one potential well is even smaller.

A PREFERRED MODEL

Various models can be constructed to aid in selecting operational parameters for the method of this invention and design parameters for the device of this invention. For example, the exact spatial and temporal structure of the electric potential generated by the electrodes actually used and the exact motion of charged particles in the separation medium subject to such a potential may be determined by the solving known differential equations of electromagnetism and particle motion. These equations can be numerically solved by standard methods (Press et al., 1992, *Numerical Recipes in C,* 2nd ed., Cambridge Univ. Press, New York (a cookbook of numerical procedures). Instead, it is preferred to construct an approximate model, which gives adequate results, and to optimize parameters based on experiments with actual devices. This preferred method results in adequate accuracy for operational and design parameters with less time and expense than an exact model.

The preferred approximate model describes the method and device of this invention as a random walk with drift. See, e.g., Wax, ed, 1954, *Selected Papers on Noise and Stochastic Processes,* Dover Publishers, New York. The random walk component is due to particle diffusion when the potential is off, and the drift component is imposed by particle trapping in potential minimums when the potential is on. The preferred model is herein described with reference to a preferred generally sawtooth-shaped electric potential, characterized by distances L and R, and with all particles initially trapped in one potential well in a loading zone. Then, the drift in the direction of separation during each cycle of the potential is $\alpha_D L$, where $\alpha_D$ is the probability for a particle of diffusion constant D to diffuse a distance R into the nearest potential well. Under the preferred parameter constraints, the probability that particles diffuse backward or forward by more than one potential well is negligible. The variance of particle position increases per potential cycle according to $(\alpha_D - \alpha^2_D)L^2$. The central limit theorem shows that the concentration profile of the particles as observed over many potential wells becomes a Gaussian distribution. See, e.g., Wax, ed, 1954, *Selected Papers on Noise and Stochastic Processes,* Dover Publishers, New York.

Therefore, after a time, t, that is after tf cycles, the Gaussian distribution of particle concentration has a peak, called $<x_D(t)>$, given by:

$$\{x_D(t)\}=tf\alpha_D L \quad (5)$$

The half-width of the Gaussian distribution of particle concentration, called $\delta x_D(t)$, is given by:

$$[\{\delta x_D^2(t)\}]^{1/2}=[\{x_D(t)L(1-\alpha_D)\}]^{1/2} \quad (6)$$

These expressions characterize the particle concentration across several potential wells.

Since the particles diffuse freely when the potential is off, $\alpha_D$ can be calculated as the fraction of particles that diffuse at least a distance R to the right during time $t_{off}$. According to standard diffusion theory, this is given by $$\alpha_D = \frac{1}{2} \text{erfc}(R / \sqrt{4Dt_{off}}) \quad (7)$$

See, e.g., Wax, ed, 1954, *Selected Papers on Noise and Stochastic Processes,* Dover Publishers, New York. In this expression, the complementary error function is defined by $$\text{erfc}(x) = (2/\sqrt{\pi}) \int_x^\infty dt \exp(-t^2). \quad (8)$$

Polynomial approximations for erfc(x) are found in Abramowitz et al., 1972, *Handbook of Mathematical Functions,* Dover Publishers, New York. Eqn. 7 for $\alpha_D$ assumes that the initial distribution of particles in each potential well is of very small width. In fact, the initial distribution of the particle density trapped in the bottom of each well when the potential has finite width, is on the order of the width of an electrode. However, this difference affects only the numerical predication of $\alpha_D$. It does not affect the model, in particular, Eqns. 5 and 6, since all these require that $\alpha_D$ functionally depend in a known manner on the diffusivity, D.

This model demonstrates how particle species of different diffusivities are separated by this invention. First, eqns. 5 and 7 demonstrate that a species with a greater diffusivity is transported in the direction of separation more rapidly than a species with a lesser diffusivity. Eqn. 5 also demonstrates that the separation between species of different diffusivities grows linearly with time, t, or equivalently the number of cycles, $N_{cyc}$. Second, Eqn. 6 demonstrates that the widths of the concentration profiles of each species increase as $t^{1/2}$. Since the separation between concentration profiles for each species grows more rapidly than the widths of the concentration profiles of any species, after a sufficient number of potential cycles the concentration peaks associated with species of different diffusivities becoming spatially separated in an observable manner.

Moreover, Eqn. 7 demonstrates how the time required for separation depends on device feature size. The shape of the concentration profiles of the species and the rate of separation of the species are determined entirely by the probability parameter $\alpha_D$. As this parameter, in turn, depends only on the argument of the complementary error function, a change in the feature size R can be balanced by a change in the time $t_{off}$ that leaves this argument unchanged. Since R enters linearly and $t_{off}$ enters as a square root, a 2× reduction in the feature size permits a 4× reduction in the time required for a separation. The overall length of the device scales linearly with R (at constant R/L). Therefore, separations are increasingly rapid for sufficiently small device length. Thus, advances in microfabrication technologies can be applied to enhance directly the performance of the device by reducing its feature size. The devices should remain larger than the previously discussed minimum, i.e., an order of magnitude larger than the size of the particles to be separated.

Figure 11A:
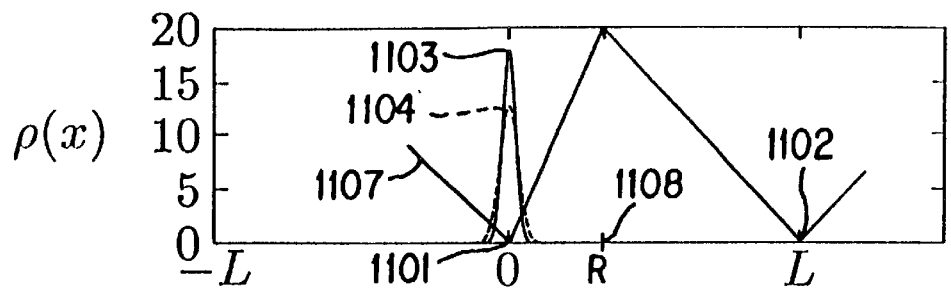
FIGS. 11A–11D illustrate in detail form the behavior of the particle concentration profile in two adjacent potential wells in the method of FIGS. 9A–9E.
Figure 11B:
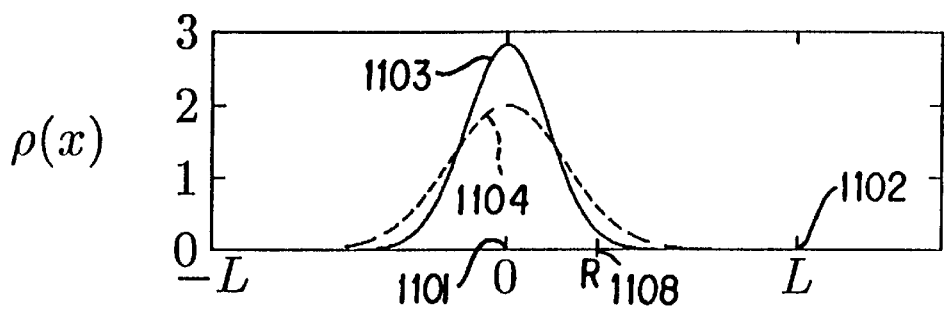
Figure 11C:
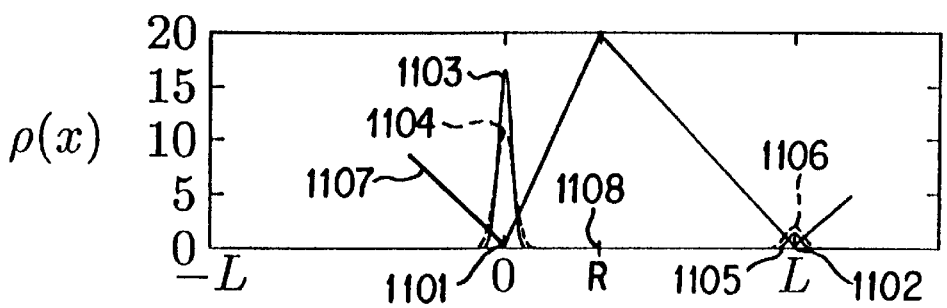
Figure 11D:
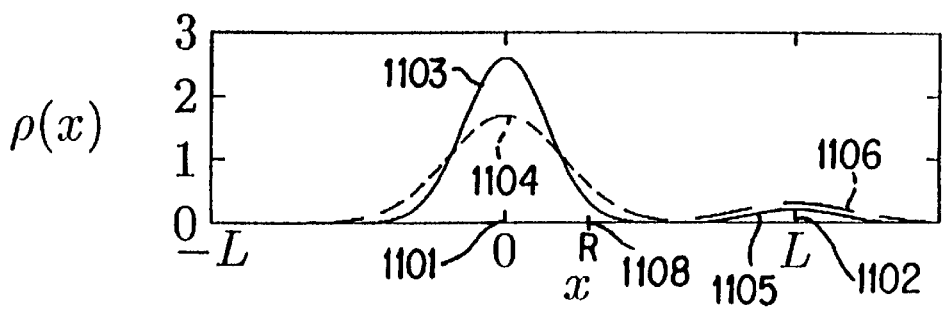

FIGS. 11A–D and 12A–E illustrate the operation of the invention according to this model. FIGS. 11A–D illustrates the detailed concentration profiles of two species of particles, A and B, of differing diffusivities, species B having greater diffusivity than species A, in two adjacent potential wells, generally indicated at 1101 and 1102. Position 1108, also labeled R, is the nearest potential maximum adjacent to minimum 1101. In FIG. 11A, electric potential 1107 is on and the particles are attracted to initial potential well 1101 and tightly trapped against thermal spreading according to Eqn. 2. Concentration profiles 1103 of species A and 1104 of species B are generally Gaussian-like in each well. In FIG. 11B, the electric potential is turned off and the molecules diffuse at rates dependent on their diffusivities in both directions in the separation medium. Species A and B now have broader Gaussian-like concentration profiles, 1103 and 1104, with profile 1104 of species B being broader as it has greater diffusivity. Some of species A, profile 1103, and more of species B, profile 1104, diffuse beyond adjacent maximum 1108. In FIG. 11C, potential 1107 is turned on again and the particles again are attracted and tightly trapped in wells 1101 and 1102. However, now those particles that diffused beyond maximum 1108 are trapped in well 1102 in concentration profiles 1105 of species A and 1106 of species B. These particles have drifted one well forward. More of species B than of species A is in well 1102. In FIG. 11D, the potential is turned off again and both species diffuse outward from both wells. Due to the asymmetry of the potential, the concentration profile of the molecules has been selectively transported to the right with the species of greater diffusivity being transported faster.

Figure 12A:
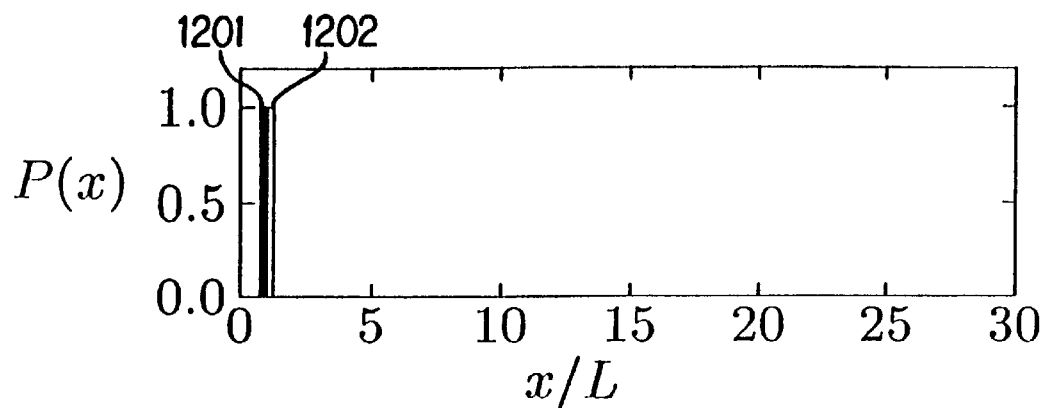
FIGS. 12A–12E illustrate in detail form the behavior of the particle concentration profile in a plurality of adjacent potential wells in the method of FIGS. 9A–9E.
Figure 12B:
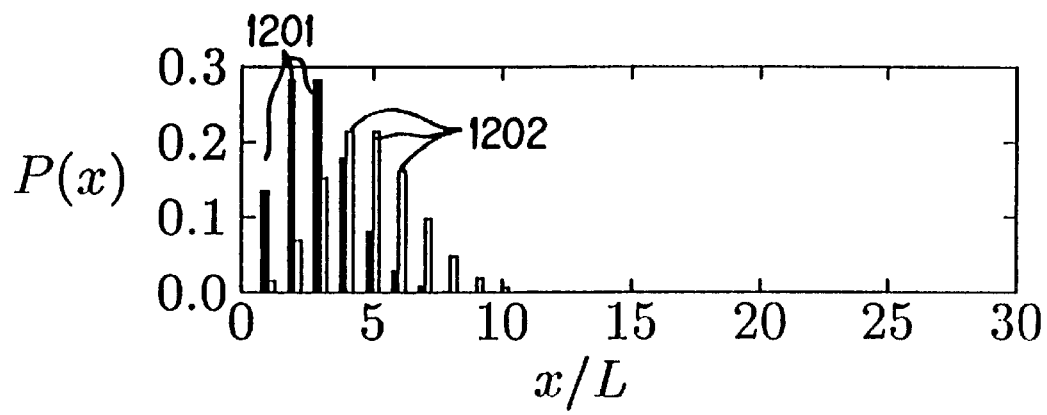
Figure 12C:
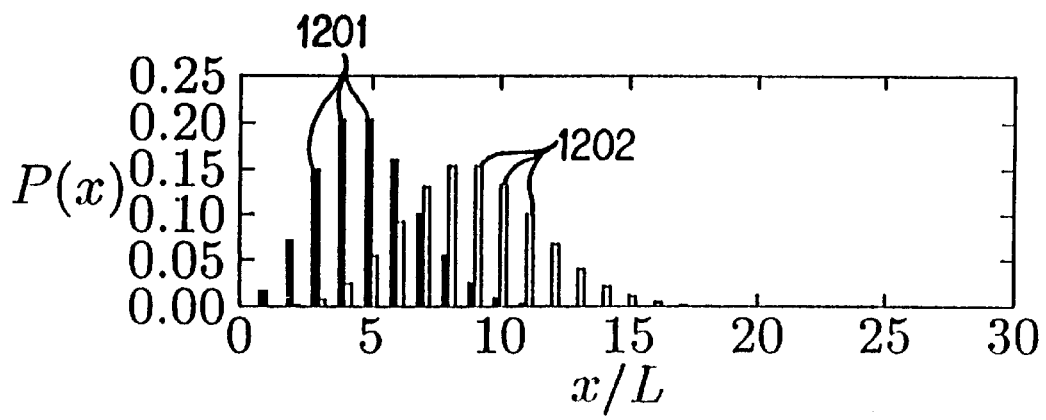
Figure 12D:
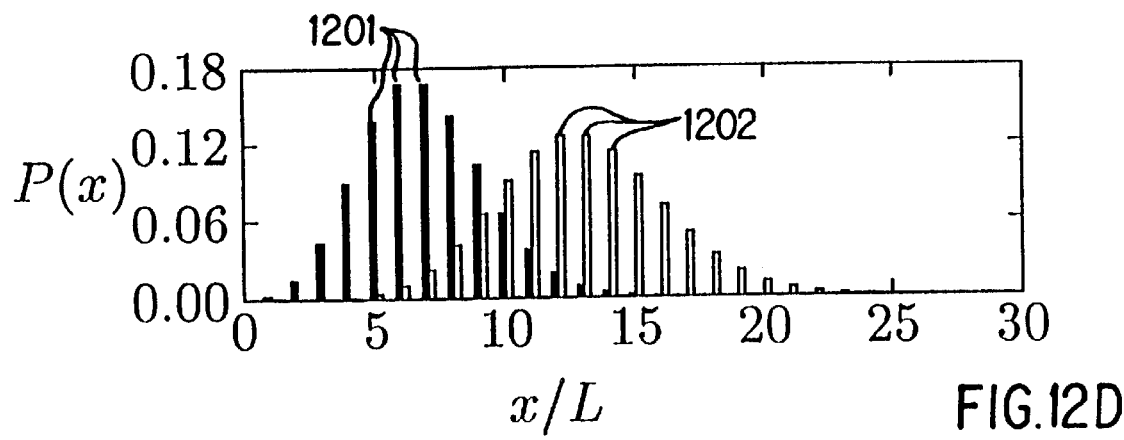
Figure 12E:
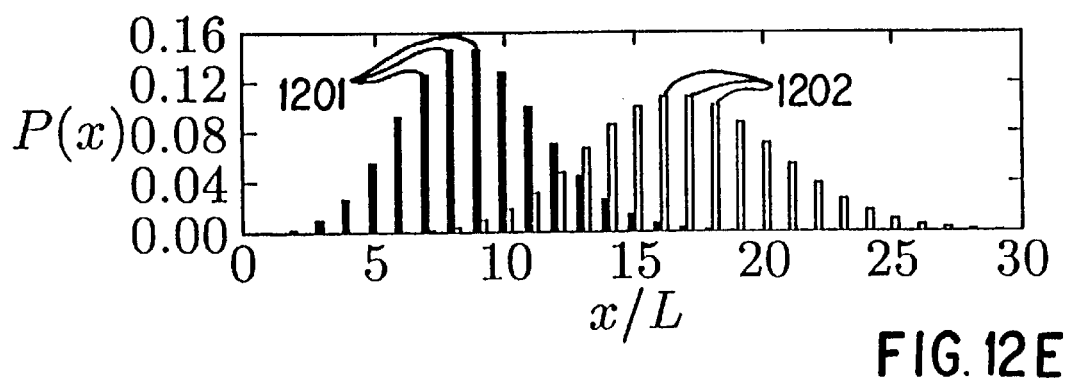

FIGS. 12A–E illustrates the operation of the model of the invention on a scale of many potential wells. These figures are generated from an exact calculation based on the random walk with drift model. The horizontal axis is along the direction of separation and includes 30 potential wells. The vertical axis represents the concentration of the two species of charged particles to be separated, species A and B. Species A, of lesser diffusivity, is represented by bars 1201, and species B, of greater diffusivity, is represented by bars 1202. The time $t_{on}$ and $t_{off}$ are chosen optimally according to methods to be described. FIG. 12A illustrates the initial condition in which both species are trapped in the first potential well only. FIGS. 12B, 12C, 12D, and 12E show the concentration profiles of both species after 25, 50, 75, and 100 cycles, respectively. These profiles become increasingly Gaussian over many potential wells as the number of cycles increases, as required by the central limit theorem. From FIGS. 12B–E, it is apparent that species B is transported to the right faster than species A and that both concentration profiles spread over time. It is also apparent the species are being separated since the concentration peaks are moving apart faster than the concentration profiles are spreading.

5.3.2. Choice Of Optimum Parameters

Optimal selection of method operating parameters and device design parameters depends on which characteristics of the particle separation are to be optimized. This section describes a method for minimizing the separation time according to the preferred model. It will be apparent that the same method can be applied to more realistic device models incorporating more structural details of the device, the potential, and particle transport. Alternately, in an analogous manner according to both the preferred model and more complete models, one of average skill in the art can optimize other separation characteristics, such as, for example, the spatial distance of separation.

The preferred operating parameters are chosen to minimize total separation time, which is determined by the potential cycle time, $t_{on}+t_{off}$. This section describes, first, the optimization of $t_{on}$ and related parameters, and second, the optimization of $t_{off}$ and related parameters.

Parameters selected by these methods are necessarily approximate. More accurate optimal parameters can be determined from the parameters herein determined by routine experimentation with actual devices. Further, an actual device need not be operated at the exactly optimal parameters determined according to any method. One of skill in the art will recognize that an actual device can be operated with parameters deviating slightly or substantially from the exactly optimal in order to accommodate, for example, the characteristics of the available equipment, inaccuracies in setting operating parameters, etc. It is only preferable to operate a device near the determined parameters in order to achieve the optimums.

The methods described herein are capable of implementation as a computer program by routine translation into an appropriate computer language, such as C, Basic, Fortran, etc. This computer program can command a general purpose computer system to perform the parameter selection methods described. Such a computer system can be, for example, an IBM or equivalent PC. Accordingly in one embodiment, this invention provides a process for selecting optimum parameters for the separation of charged particles along a direction of separation in a separation medium exposed to an electric potential, the process comprising: (a) inputting diffusivities of the charged particles and one or more electrical breakdown parameters of the separation medium; (b) calculating a first optimum time of an on-condition of said potential, wherein said electric potential has a stationary spatial pattern comprising a plurality of potential wells disposed along the direction of separation, each said well having a potential minimum, and has a time-varying amplitude comprising repeated variations between at least two conditions, said on-condition in which the charged particles are attracted to said potential minimums of said potential wells and an off-condition in which the charged particles can diffuse in said separation medium; (c) calculating a second optimum time of said off-condition of said potential as the time that minimizes a total separation time of the charged particles; and (d) outputting said first and second optimum times.

Further, this invention also provides a computer system which carries out the above process, and for a computer readable medium embodying a program for carrying out the above process. Additionally, this invention provides that the devices described in Section 5.1 can optionally be accompanied by the above computer readable medium for selecting the operational parameters of the devices.

Figure 18:
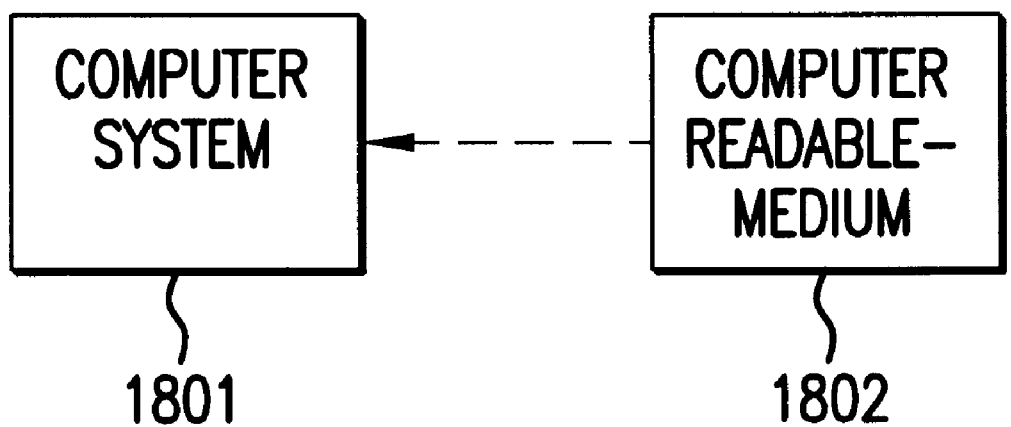
FIG. 18 illustrates an exemplary computer system and an exemplary computer readable medium.

FIG. 18 illustrates exemplary computer system 1801, which can be an IBM PC or equivalent, for carrying out the above process, as well as exemplary computer readable media 1802, for embodying a program for carrying out the above process. As indicated, computer system 1801 is capable of reading computer-readable medium 1802.

PREFERRED OPTIMIZATION OF $t_{on}$ AND RELATED PARAMETERS

It is preferable to select operational and device parameters so that $t_{on}$ is as small as possible. Here, first, relations relating $t_{on}$ to relevant parameters are determined according to the preferred model, and second, these relations are used to determine optimal values for these parameters.

The time $t_{on}$ is the time for a charged particle to drift in the direction of separation under the influence of the potential from a maximum in the potential to the subsequent minimum, a distance L−R. For example, in FIG. 10, $t_{on}$ is the time for a particle to drift from 1001 to 1003. This time is given by:

$$t_{on} = (L-R)/V_{drift} \qquad (9)$$

where $V_{drift}$ is the drift velocity of a particle in the potential.

Since the motion of a particle in the separation medium is over-damped, $V_{drift}$ is proportional to the force from the electric potential times a friction coefficient, and is given by $$V_{drift} = \gamma Q \left( \frac{V_o}{L-R} \right). \qquad (10)$$

Note that since the potential must be eccentric, R<L/2. The electric field E in the pertinent region of drift is $-V_0/(L-R)$. The friction coefficient, γ, is related to the diffusion constant by a fluctuation-dissipation theorem $$\gamma = D/k_B T. \qquad (11)$$

See, e.g., Wax, ed, 1954, *Selected Papers on Noise and Stochastic Processes,* Dover Publishers, New York. Combining these equations, $t_{on}$ is given by $$t_{on} = \frac{k_b T(L-R)^2}{QDV_o} \qquad (12)$$

Therefore, according to Eqn. 12, given L−R, the minimum and hence most preferable $t_{on}$ can be calculated. Further, $V_o$ should be selected to be as large as possible consistent with the electric field remaining less than the breakdown field and electrolysis threshold of the separation medium used. The maximum electric field, $E_{max}$ arises along the steeper side of the potential and is given by $$E_{max} = \frac{V_o}{R} \qquad (13)$$

Optimally, the device should be operated as close to the limiting field as possible. In this case, $t_{on}$ is given by $$t_{on} = \frac{k_b T(L-R)^2}{QDRE_{max}}. \qquad (14)$$

For example, in the case of water the limiting breakdown field is approximately $10^4$ V/cm (Avallone at al. eds., 1987, *Marks' Standard Handbook for Mechanical Engineers,* McGraw-Hill, New York, pp. 15–19). Therefore, if $E_{max}=10^4$ V/cm and R=1 μm, then the maximum $V_0$ is 1 V.

PREFERRED OPTIMIZATION OF $t_{off}$ AND RELATED PARAMETERS

In order to optimally select $t_{off}$ and related parameters it is necessary to specify what is meant by a successful separation of a particle type of diffusivity D from a type of diffusivity D+ΔD. In this section, it is assumed that ΔD is much less than D. A preferred separation specification is that separation occurs when the difference between the exit times from the device of the concentration peaks of the two types of particles is at least as large as the spreading of the concentration peaks. In this case, the concentration profiles of the two types of particles can be experimentally distinguished. Alternatively expressed, separation occurs at that time, or number of cycles, when the difference in positions of the concentration peaks of the two types of particles is at least as large as the Gaussian spreading of the two peaks. For example, in FIGS. 12A, 12B, and 12C the two concentration peaks would not be considered as separated according to this preferred specification. However, in FIGS. 12D and 12E the peaks would be considered as separated. Alternative more or less stringent separation specifications can be applied to select operational parameters. A less stringent condition might consider, for example, FIG. 12C as also separated.

According to this preferred separation specification, separation occurs at a time $t_D$ given by:

$$\{x_D(t_D)\} - \{x_{D+\Delta D}(t_D)\} = [\{\delta x_D^2(t_D)\}]^{1/2} \tag{15}$$

Here, upon exiting the device after time $t_D$, the time required for a particle of diffusivity D to traverse the device, the concentration profiles of the two types of particles are separated.

From Eqns. 5 and 6, the separation condition can be written as $$t_D f(\alpha_D - \alpha_{D+\Delta D}) L = \sqrt{t_D f \alpha_D L^2 (1-\alpha_D)}, \tag{16}$$

where $\alpha_D$ is the probability that a particle of diffusivity D diffuses to the next potential well during $t_{off}$. $\alpha_D$ is given by Eqn. 7, which is repeated here for convenience.

$$\alpha_D = \frac{1}{2} erfc \left( R / \sqrt{4Dt_{off}} \right) \tag{17}$$

From Eqn. 16, the number of cycles, $N_{cyc}(=t_N f)$, required to separate particles of diffusivity D from particles of diffusivity D+ΔD is given by:

$$N_{cyc} = \alpha_D (1-\alpha_D)/(\alpha_D - \alpha_{D+\Delta D})^2. \tag{18}$$

The difference $\alpha_D - \alpha_{D+\Delta D}$ can be approximated as $-\Delta D \partial \alpha_D / \partial D$ for sufficiently small ΔD. The total separation time is:

$$T_{tot} = N_{cyc}(t_{on} + t_{off}) \tag{19}$$

The preferred optimum parameters are selected to minimize $T_{tot}$. Operational and device parameters have previously been selected to minimize $t_{on}$. $T_{tot}$ depends on $t_{off}$ both directly, through Eqn 19, and indirectly, since $N_{cyc}$ depends on $\alpha_D$ which in turn depends on $t_{off}$. To select the optimum value of $t_{off}$, all these equations must be minimized together. This minimization is most easily done by standard numerical methods, for example, by systematically trying various values for $t_{off}$ until a minimum is found. See, e.g., Press et al., 1992, *Numerical Recipes in C*, 2nd ed., Cambridge Univ. Press, New York. An example of the selection of an optimum $t_{off}$ is given in Sec. 5.4 for the case of DNA fragment separation.

Once optimum $t_{off}$ and $N_{cyc}$ values have been selected, the total device length required for separation is given by $$L_{tot} = \{x_D(t_D)\} = N_{cyc} \alpha_D L. \tag{20}$$

The preferred optimum quantities selected depend on the spatial characteristics of the potential.

PREFERRED OPTIMIZATION OF L AND R

The preceding optimization of $t_{on}$ and $t_{off}$ assumed that R and L are fixed. If these lengths can be varied they should be selected in view of the previous optimum time parameter determinations. First, in view of Eqn. 14, L should be selected as small as possible. Second, in view of Eqn. 17, since a 2× reduction in R allows a 4× reduction in the $t_{off}$, R should be chosen as small as possible. Third, to have sufficient eccentricity of the potential wells, it is preferable that R/L<0.3. And fourth, R and L are limited to be at least as large as the minimum dimensions permitted by a chosen fabrication technology. These conflicting requirements on R mean that for a chosen separation medium with a fixed $E_{max}$ ($V_o$ being varied) an optimum R exists.

In a preferable method for optimization, the separation time $T_{tot}$ is minimized as a function of L and R, subject to the constraint that the resulting device sizes can be fabricates by the chosen fabrication technologies. An additional constraint is that for each value of L and R, it is optimum to select the applied potential, $V_o$, such that the electric fields are smaller than the breakdown field, $E_{max}$. For this value of $V_o$, the times $t_{on}$ and $t_{off}$ are selected in an optimum manner, as described previously, to arrive at an optimum $T_{tot}$ for given L and R. Using multidimensional minimization techniques that are well-known to those of average skill in the computational arts (Press et al., 1992, *Numerical Recipes in C*, 2nd ed., Cambridge Univ. Press, New York) the optimum pair of L and R is then readily and preferably determined from this optimization problem.

In another method, the optimum R can be determined by the simultaneous minimization, within the technology allowed bounds, of Eqns. 14, 17, 18, and 19. This can be preformed by standard numerical techniques from Press et al. Alternatively, this minimization can be performed by the following simple search procedure. Pick an initial R at the minimum allowed bound and determine an optimum $T_{tot}$ by the previous methods. Increase R by some fraction, say 5%, and repeat the determination of an optimum $T_{tot}$. For all determinations of $T_{tot}$, chose the maximum value of $V_o$ that can be applied in the given separation medium selected. Continue this iteration until a minimum value for $T_{tot}$ is found, either at the lower bound on R or at an intermediate value of R. The preferred value of R is the one that minimizes $T_{tot}$. Having chosen R, L can be preferably determined so that R/L has a fixed value providing sufficient eccentricity of the potential wells. Preferably R/L is less than 0.3, and more preferably is approximately 0.1.

For all of the sample calculations below, the optimum values are assumed to be R=1 μm and L=10 μm, unless specified otherwise. A potential with this periodicity is readily produced by common microfabrication techniques, such as those described in Sec. 5.5.

Finally, the separation medium should be chosen in order that the particles to be separated are suspended in the medium in a charged state and have differing diffusivities when suspended. The greater the difference in diffusivities, the more preferable is the medium. It is further preferable that the separation medium be chosen from among the otherwise suitable mediums to have a relatively high $E_{max}$ and a relatively high electrolysis voltage compared to the other suitable mediums. Here, relatively high can be taken to be at least greater than the average values for the otherwise suitable mediums. These conditions permit a minimum $t_{on}$. Finally, it is preferable that the separation medium have low ionic strength to minimize screening of the potential wells.

5.3.3. The Case Of Widely Varying Diffusivities

The preceding sections have described a preferred model, and the determination of preferred operating and device parameters in view of the model, for the case where the particles to be separated have similar diffusivities. This invention is also applicable to mixtures which contain particles with widely varying diffusivities.

One mode of operation to separate such mixtures is to begin the with $t_{on}$ and $t_{off}$ at the short times optimal for separating particles of higher diffusivities. With these times, the more diffusive particles are rapidly separated. However, the particles of lower diffusivities, having much smaller $\alpha_D$ values, remain nearly stationary. After the more diffusive particles have been separated, the times $t_{on}$ and $t_{off}$ are increased to the larger values optimal for separation of the less diffusive particles. The less diffusive particles are then rapidly separated subsequently.

Another mode of operation to separate such mixtures is to use the longer $t_{on}$ and $t_{off}$ times appropriate for the less diffusive particles. With such longer times, the more diffusive particles have larger $\alpha_D$ values and may be able to diffuse more than one potential well in the forward direction as well as in the backward direction. The previous model assumed that particles to be separated either did not move or diffused at most one potential well in the forward direction during $t_{off}$. However, a similar model based on random walk with drift can be constructed for the case in which some of the particles to be separated diffuse more than one potential well during $t_{off}$.

To construct such a model, define $\alpha_D^{(n)}$ as the probability that a particle with diffusivity D diffuses n potential well during the time $t_{off}$ for free diffusion. According to standard diffusion theory in a manner similar to that of Eqn. 7, this $\alpha$'s are given by $$\alpha_D^{(n)} = \frac{1}{\sqrt{4\pi D t_{\text{off}}}} \int_{R+(n-1)L}^{R+nL} dx \exp(-x^2/4Dt_{\text{off}}). \tag{21}$$

When the diffusivity, D, is relatively small compared to $t_{off}$, $\alpha_D^{(1)}$ rapidly approaches the value for $\alpha_D$ of Eqn. 7. In this case, $\alpha_D^{(1)}$ and $\alpha_D^{(o)}$ (the probability that the particles stay put) are the only non-zero $\alpha_D^{(n)}$, implying that the particle either stays put or diffuses forward by a single potential well spacing. However, when the diffusivity is relatively large, $\alpha_D^{(n)}$ for n=-1, 2, etc., can become important.

To model the invention in the case that particles can diffuse more than a potential well during $t_{off}$, redefine the parameter $\alpha_D$ as the effective probable diffusion distance $$\alpha_D = \sum_{n=-\infty}^{\infty} \alpha_D^{(n)} n. \tag{22}$$

With this definition, the average position of the maximum of the Gaussian-like particle concentration profile, again called $<x_D(t)>$, is given by $$\{x_D(t)\} = t f \alpha_D L \tag{23}$$

This is the same as Eqn. 5 of the previous model, where the particles were assumed to diffuse by one potential well at most.

The variance in the Gaussian-like particle concentration profile of particles of diffusivity D after total time t, again called $\delta x_D(t)$, is equal to the number of diffusion cycles in time t, that is tf, times the variance change $<\delta x_D^2>$ for a single cycle, which is in turn given by $$\langle \delta x_D^2 \rangle = \langle x_D^2 \rangle - \langle x_D \rangle^2 \tag{24}$$
$$= \sum_{n=-\infty}^{\infty} \alpha_D^{(n)} n^2 L^2 - \alpha_D^2 L^2$$

Again, the preferred condition defining the occurrence of separation of particles of diffusivity D from particles of diffusivity D+$\Delta$D, where now $\Delta$D is of the order of magnitude of D or larger, is that distance between the concentration peaks must be at least as large as the half-width of the concentration profile. From Eqns. 23 and 24, this condition for separation is given by $$N_{cyc}L(\alpha_D - \alpha_{D+\Delta D}) = \sqrt{N_{cyc}\langle \delta x_D^2 \rangle}. \tag{25}$$

These equations permit the same conclusion for this case, where $\Delta$D is of the order of D or larger, as for the previous case where $\Delta D << D$. As previously, Eqns. 21 and 23 demonstrate that particles of greater diffusivity are transported more rapidly through the device than particles of lesser diffusivity and that the distance between the concentration peaks increases linearly with time. Eqn. 25 demonstrates that peaks of different diffusivities are separated. Again, separation occurs since the distance between the concentration profiles grows linearly with $N_{cyc}$ while the width of the concentration peaks grows only as the square root of $N_{cyc}$. Further, because of the behavior of Eqn. 21, the separation time is decreased by 4× for every 2× reduction in the spatial scale of the potential.

Further, operational parameters optimizing $t_{on}$ can be selected in a manner similar to the previous case. For example, $N_{cyc}$ is given by $$N_{cyc} = \frac{\sum_{n=-\infty}^{\infty} \alpha_D^{(n)} n^2 - \alpha_D^2}{(\alpha_D - \alpha_{D+\Delta D})^2} \tag{26}$$

This corresponds to the form of Eqn. 18. Therefore, the $t_{off}$ that minimizes $T_{tot}$ can obtained by numerical minimization of Eqns. 19, 21, 22, and 26, similarly to the previous case in which the particles diffused at most by one potential well during $t_{off}$.

Thus mixtures of particles with widely varying diffusivities can be separated by the method even if operational parameters are chosen so that the more diffusive particles diffuse more than one potential well during $t_{off}$. In one mode of operation for separating such mixtures, the cycling times $t_{on}$ and $t_{off}$ can be first optimized for rapid separation of the more diffusive particles, and then gradually increased to larger values optimized for the separation of less diffusive particles. In a second mode of operation, the cycling times can optimized to separate the largest fragments, still providing an adequate separation for the smaller fragments.

5.3.4. Alternate mode of operation: multiple states

Another mode of operation consists of cycling the potential through three states instead of two states. These three states include the following steps:

1. turning the potential on;
2. briefly reversing the potential one or more times during the on-condition; and
3. allowing free diffusion.

Briefly reversing the potential one or more times during the on-condition can be effective in reducing the electrostatic screening from an ionic double layer formed by small, highly mobile counterions attracted to the potential wells or electrodes. These counterions can be displaced and the double layer minimized by interspersing with $t_{on}$ several rapid pulses in which the polarity of the potential is reversed. Preferably, the period of reversal is sufficiently small such that, although there is substantially no effect on the distribution of the larger, less mobile particles, the highly mobile, smaller counterions are displaced out of the potential wells or in a reverse direction from the electrodes. This is accomplished by satisfying the inequality $t_{pulse} \ll t_{on}$, $t_{off}$.

Another three-state mode of operation uses a third stat with a sharp, substantially symmetric V-shaped potential centered at the bottom of each potential well, such as may be created by a third electrode between the two sets of electrodes present in device types I and II. The electrodes of this embodiment are located at relative positions −R, O, and R, with a periodicity of L. In the first state, which lasts for time $t_{on}$, the electrodes at relative position O are charged to $V_o/2$ and the electrodes at relative position R are charged to $-V_o/2$. In the third state, which lasts for time $t_{off}$, the electrodes are all uncharged and the particles diffuse freely. These first and third states are identical to the two states of the mode of operation described in previous sections. In the additional, third, middle state, the electrodes at relative positions −R and +R are charged to $+V_o/2$, and the middle electrodes at relative positions O are charged to $-V_o/2$. This creates a narrow V-shaped potential well, which tightly localizes the particles.

This is useful because it can provide a stronger and narrower trap for particles at the bottom of a potential well with steep walls on either side. This will produce a density distribution in each well in each potential cycle closer to the preferable vanishingly thin distribution.

5.4. Application to DNA Separation

An important application of the invention is to separate biopolymers (including biopolymer fragments), in particular, nucleic acids such as DNA (e.g., cDNA, genomic DNA, synthetic DNA) and RNA. This application is possible because the diffusivity of DNA depends almost entirely on the number of nucleotides in the DNA molecule. There is an additional insubstantial dependence of the diffusivity on the total base composition, i.e., for dsDNA the A+T to G+C ratio.

The required separation resolution depends on the application of DNA separation, ranging from a resolution of single base pairs to a resolution of as great as 10% of total DNA length or more. For example, for DNA sequencing, perhaps the more familiar application, DNA generally must be separated with a single base or base-pair resolution. Thus, aliquots of DNA generated by standard sequencing reactions (e.g., F. Sanger et al., 1977, *Proc. Natl. Acad. Sci. USA* 74:5463; M. Maxam et al., 1977, *Proc. Natl. Acad. Sci. USA* 74:560) can be subjected to the separation methods of the invention. Another application of DNA separation, called sizing, requires a resolution of only ±5% or ±10% of the fragment length. Sizing is used to produce quickly a pattern, or fingerprint, of the sizes in a DNA mixture, such as might be generated for a RFLP determination, genotyping, linkage analysis, microsatellite analysis and other fragment analysis application.

5.4.1. Diffusivity of DNA

The diffusion constants of ssDNA and dsDNA, used for selection of operating and device parameters, can be estimated from Stokes' law or obtained from experiment. The Stokes' law diffusion constant for particles is given by $$D = k_B T / 6\pi \eta \Gamma, \qquad (27)$$

in which T is the temperature, η is the viscosity of the separation medium (for example, for water, 0.01 gm/cm sec), and Γ is an effective particle radius (Doi et al., 1986, *The Theory of Polymer Dynamics*, Clarendon Press, Oxford, p. 300).

For a spherical particle, such as denatured ssDNA, Γ is identified as the radius of gyration. Scaling arguments relate the contour length of a polymer like ssDNA to its radius of gyration. In general, $\Gamma \sim N^\gamma$, where the exponent $\gamma \approx 0.6$ (see, e.g., Doi et al., supra). For a long cylinder with length a >> diameter b, such as dsDNA, one finds that $\Gamma \approx a/\ln(a/b)$. In dsDNA with N base pairs, the Stokes' Law diffusion constant with this approximation is given by:

$$D = \frac{\ln(a/b)k_B T}{3\pi \eta a} = (1/N)\ln(0.3N) \times 1.5 * 10^{-5} \text{cm}^2/\text{sec}, \qquad (28)$$

in which diameter b=10 Å and length a=3N Å. The temperature T is assumed to be 298 K. throughout.

An experimental expression for the diffusion constant is preferable and is used throughout the following. The diffusivity of dsDNA at room temperature in water is given experimentally approximately by $$D_{dsDNA} = 1.14 \times 10^{-6} N^{-1} \text{ cm}^2/s \qquad (29)$$

in which N is the number of base pairs (Weast, ed., 1987, *Handbook of Chemistry and Physics,* Chemical Rubber Publishing Co, Boca Raton, Fla., p 117). Observationally, the inverse dependence on N dominates the relatively weak ln(N) term in Eqn. 31. For ssDNA, the diffusivity is theoretically assumed to be given by $$D_{ssDNA} = 1.14 \times 10^{-6} N^{-0.59} \text{ cm}^2/s \qquad (30)$$

The scaling with N is derived from Stokes' Law, which predicts that D depends on the inverse of the effective radius. The effective radius is derived from considering that ssDNA diffusion resembles a self-avoiding walk, in which the effective radius depends on the number of bases as $N^{0.59}$. See, e.g., Doi et al., supra.

5.4.2. Optimal Selection Of $t_{on}$ And $t_{off}$

PREFERABLE DETERMINATION OF AN OPTIMUM $t_{on}$ $t_{on}$, the time required to attract DNA fragments in the potential wells, can be determined by combining Eqns. 12 or 14 for $t_{on}$ with Eqns. 29 and 30 for the diffusion constant of DNA. The charge on DNA, Q, is $-N |e^-|$ for ssDNA and $-2N |e^-|$ for dsDNA, where N is the number of bases or base pairs and $|e^-|$ is the magnitude of the electronic charge. With $V_0$ in volts and (L−R) in μm, $t_{on}$ is given by:

$$t_{on} = \frac{(L-R)^2}{(V_o/2)N^{0.41}} \times 1.1 \times 10^{-4} \text{sec, ssDNA;} \qquad (31)$$

$$t_{on} = \frac{(L-R)^2}{(V_o/2)} \times 5.6 \times 10^{-5} \text{sec, dsDNA;} \qquad (32)$$

If $V_o$ is selected as the breakdown voltage for water, then $t_{on}$ is given by:

$$t_{on} = \frac{(L-R)^2}{RN^{0.41}} \times 2.3 \times 10^{-4} \text{sec, ssDNA; and} \qquad (33)$$

$$t_{on} = \frac{(L-R)^2}{R} \times 10^{-4} \text{sec, dsDNA,}$$

with L and R in μm.

Table 2 shows $t_{on}$ in seconds for a device with L=10 µm, R=1 µm, and $V_0$=1 V. For the preferred most rapid separation, $t_{on}$ should be chosen to be as small as possible.

TABLE 2

| Fragment Size | $t_{on}$ for ssDNA (secs) | $t_{on}$ for dsDNA (secs) |
|---|---|---|
| 10 | 0.0071 | 0.0091 |
| 100 | 0.0028 | 0.0091 |
| 500 | 0.0014 | 0.0091 |

The time $t_{on}$ scales linearly with the spatial scale of the potential (R and L). It scales differently with N for ssDNA and dsDNA. For ssDNA, since the driving force increases linearly with the molecule length, but the diffusivity decreases less rapidly, $t_{on}$ is a decreasing function of the molecule length. For dsDNA, since the dependence of the driving force on the molecule length exactly cancels the dependence of the diffusivity on the fragment length, $t_{on}$ is independent of molecule length.

PREFERABLE DETERMINATION OF AN OPTIMUM $t_{off}$

Preferably, an optimum $t_{off}$ is selected to minimize the total separation time $T_{tot}$. $T_{tot}$ is given by combining Eqn. 19 for $T_{tot}$ with Eqn. 18 for $N_{cyc}$:

$$T_{tot} = (t_{on} + t_{off})\alpha_D(1-\alpha_D)/(\alpha_D - \alpha_{D+\Delta D})^2. \quad (34)$$

The dependence of $\alpha_D$ on D and $t_{off}$ is given by Eqn. 7, which is repeated here:

$$\alpha_D = \frac{1}{2}\mathrm{erfc}\left(R/\sqrt{4Dt_{off}}\right) \quad (35)$$

D depends on N, the number of bases or base pairs in the DNA to be separated, according to Eqns. 32 and 33.

To minimize $T_{tot}$, the parameter $t_{off}$ is systematically varied to obtain a minimum value for $T_{tot}$. The parameter $t_{off}$ is optimally selected to be that value minimizing $T_{tot}$.

An exemplary program in the C language for calculating the parameters of DNA separation for this invention according to these relations, in particular Eqns. 33, 34, and 35, is set forth in Sec. 8. The input comprises the lengths R and L, the lengths N and N+ΔN for the DNA molecules to be separated, and a choice between ssDNA and dsDNA. The voltage $V_o$ is selected automatically to be the maximum consistent with the breakdown field of water and the over potential at which electrolysis of water occurs. The program can be changed for values of these parameters appropriate for other separation mediums. The program systematically varies $t_{off}$ to find the optimum $T_{tot}$. The output comprises optimum operating conditions $t_{on}$ and $t_{off}$ and further details of the operation, including $N_{cyc}$ and $T_{tot}$. The output also comprises a file containing the values of these quantities in a range about the optimum. This program can be compiled and executed on any computer system containing a C language compiler and run-time system. One skilled in the art can translate this program into other similar languages for execution on computer systems having such languages.

Figure 13:
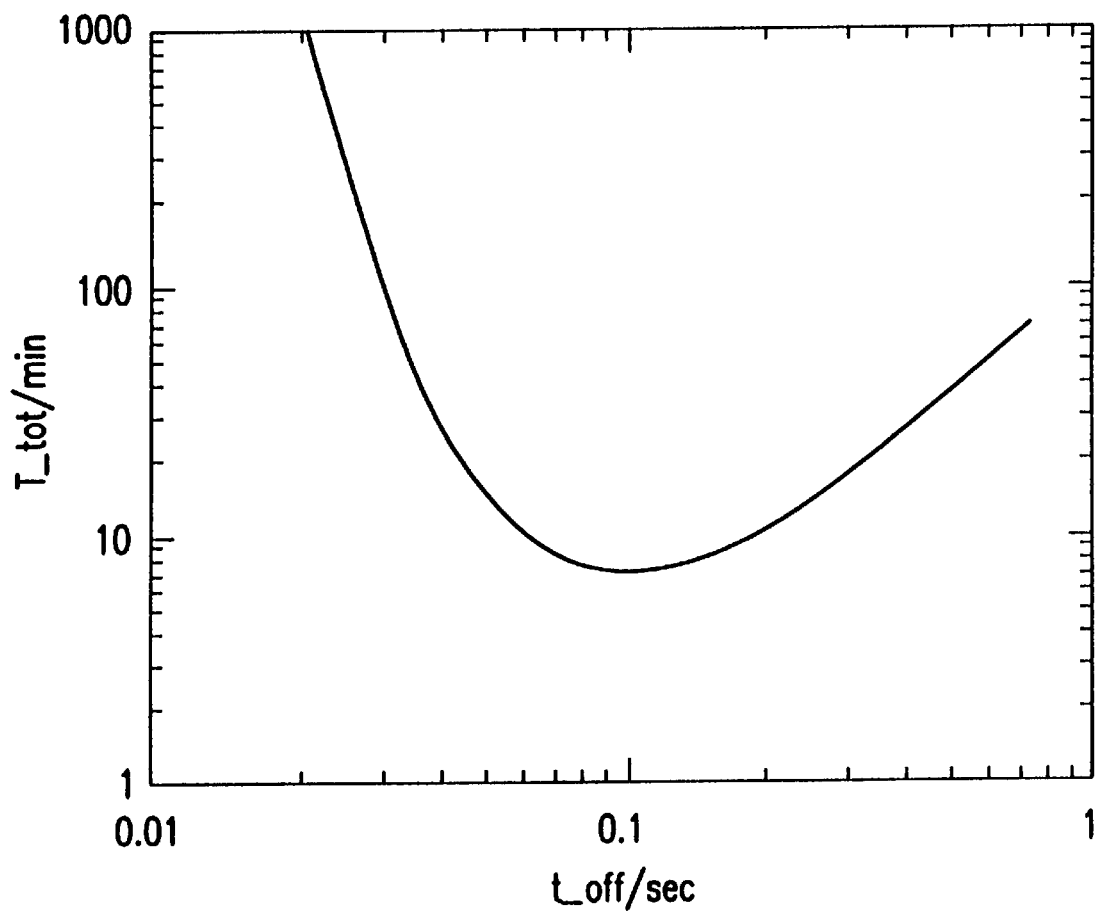
FIG. 13 illustrates the behavior of $T_{tot}$ versus $t_{off}$ for the preferred method for the selection of the operating parameters of the method of FIGS. 9A–9E.

FIG. 13 illustrates an example of the optimum selection of $t_{off}$ by the use of the program. $T_{tot}$ is numerically evaluate in terms of $t_{off}$ for a potential with L=10 µm and R=1 µm in which a dsDNA molecule of length 100 is to be separated from one of length 105 in an aqueous separation medium. FIG. 13 shows the resulting graph of the relation between these two quantities. From FIG. 13, it is evident that the optimum choice for $t_{off}$ is 0.10 sec, which yields a optimum total separation time of 6.8 min.

Table 3 presents the results of similar optimizations for a variety of DNA molecule lengths and required separation resolutions. In all cases the separation is in an aqueous medium with a potential having L=10 µm and R=1 µm.

TABLE 3

| DNA fragment | $T_{tot}$/min | $L_{tot}$/cm | $t_{off}$/sec | $N_{cyc}$ | $\alpha_N$ |
|---|---|---|---|---|---|
| ssDNA | | | | | |
| N = 10, ΔN = 1 | 0.48 | 0.083 | 0.0053 | $2.3 \times 10^3$ | 0.036 |
| N = 100, ΔN = 1 | 71. | 4.4 | 0.015 | $2.3 \times 10^5$ | 0.019 |
| N = 100, ΔN = 10 | 0.85 | 0.057 | 0.016 | $2.7 \times 10^3$ | 0.021 |
| N = 500, ΔN = 25 | 7.0 | 0.18 | 0.038 | $1.1 \times 10^4$ | 0.017 |
| N = 500, ΔN = 50 | 1.9 | 0.052 | 0.039 | $2.8 \times 10^3$ | 0.019 |
| dsDNA | | | | | |
| N = 10, ΔN = 1 | 0.32 | 0.028 | 0.013 | $8.7 \times 10^2$ | 0.032 |
| N = 100, ΔN = 1 | 150 | 1.48 | 0.098 | $8.5 \times 10^4$ | 0.017 |
| N = 100, ΔN = 10 | 1.9 | 0.021 | 0.11 | $9.9 \times 10^2$ | 0.022 |
| N = 500, ΔN = 25 | 32. | 0.067 | 0.50 | $3.8 \times 10^3$ | 0.018 |
| N = 500, ΔN = 50 | 9.0 | 0.020 | 0.52 | $1.0 \times 10^3$ | 0.020 |

Figure 14:
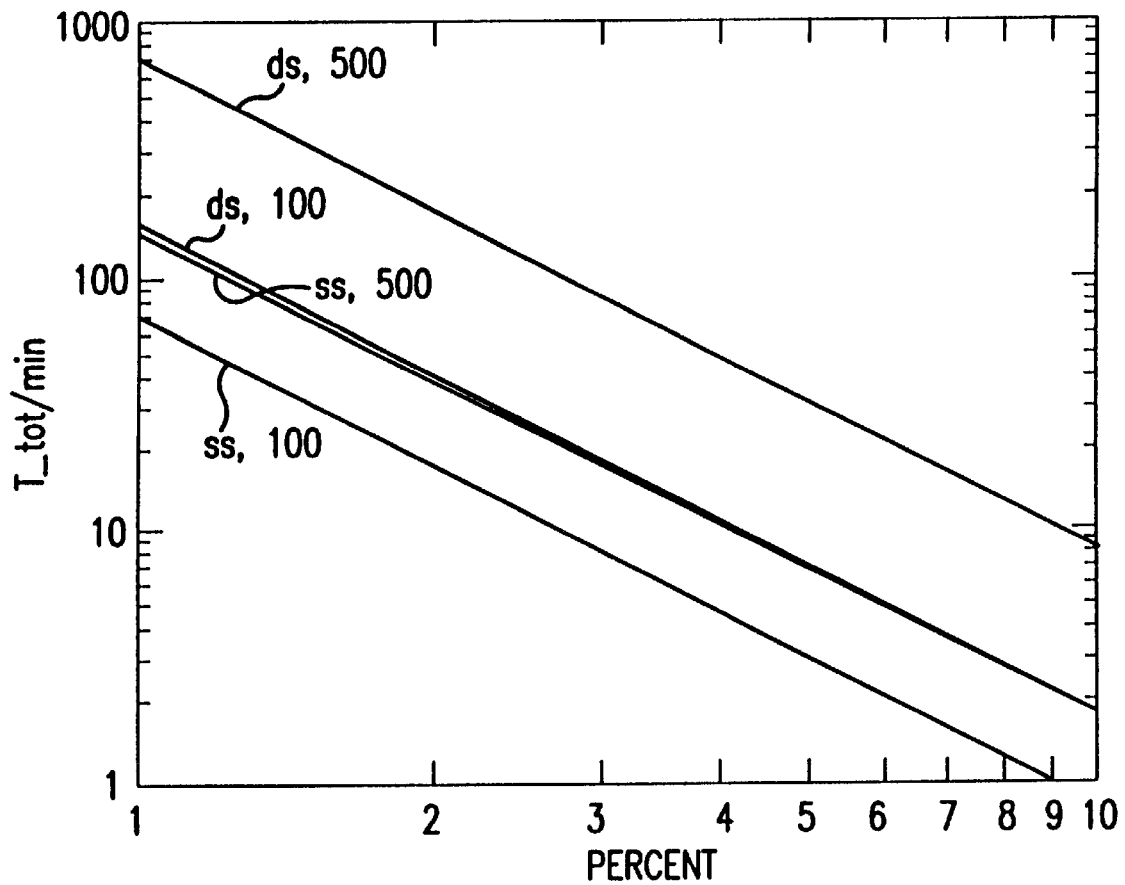
FIG. 14 illustrates the behavior of $T_{tot}$ versus the percentage of separation resolution of DNA molecules when method operating parameters are selected according to the preferred method for the selection of the operating parameters of the method of FIGS. 9A–9E.

FIG. 14 graphically presents a summary of a large number of such optimization calculations. The horizontal axis of the graph indicates the desired separation resolution, expressed as a percentage of the molecule length. The vertical axis indicates the required total separation time, $T_{tot}$, in minutes. The graphs indicate the separation times required for two molecule lengths, 100 and 500, for ssDNA and dsDNA. Again, all separation are in an aqueous medium with a potential having L=10 µm and R=1 µm.

It is evident from FIG. 14 that separations are much more rapid for sizing, requiring only a 5–10% resolution, than for sequencing, requiring a 1% or less resolution. From FIG. 14, a factor of 10 change in the required resolution leads to a factor of 100 change in $T_{tot}$. For example, separation of molecules of length 100 with a resolution of 5 bases (5%) can be performed 25 times more rapidly than the separation of molecules of length 100 with a resolution of 1 base (1%). Therefore, it can be clearly appreciated that rapid sequencing and extremely rapid sizing of DNA are possible with this device. Reducing the device size and increasing the diffusivity, for example, by changing the separation medium or by increasing temperature, shortens separation times for the device.

5.4.3. Eccentricity Of The Potential

This section describes an exemplary demonstration that a more eccentric potential is preferable for faster separation times. Optimum separation parameters are calculated for potentials with fixed a periodic length, L, of 10 µm, but with a varying R, the distance between the potential well and the nearest adjacent maximum. A smaller ratio R/L means the potential minimum is more eccentrically placed in each potential well. Table 4 presents the results of the calculations performed for separation of ssDNA fragments of length 100 with single base resolution (1%) in an aqueous medium. In all cases, we use $V_o$=2 V.

TABLE 4

| R/µm | $T_{tot}$/min | $L_{tot}$/cm | $t_{off}$/sec | $N_{cyc}$ | $\alpha_N$ |
|---|---|---|---|---|---|
| 2 | 246. | 4.0 | 0.058 | $2.5 \times 10^5$ | 0.016 |
| 1 | 66. | 4.2 | 0.015 | $2.4 \times 10^5$ | 0.017 |

TABLE 4-continued

| R/$\mu$m | $T_{tot}$/min | $L_{tot}$/cm | $t_{off}$/sec | $N_{cyc}$ | $\alpha_N$ |
|---|---|---|---|---|---|
| 0.5 | 21. | 4.9 | 0.0041 | 2.3 × 10⁵ | 0.022 |
| 0.25 | 9.5 | 6.5 | 0.0012 | 2.0 × 10⁵ | 0.032 |

The performance of the device increases, that is the total separation time decreases, as the ratio R/L decreases.

5.5. Microfabrication of Device Types I And II

A device operating according to a method of this invention may be of any physical size appropriate to the separation application and consistent with the previously described minimum sizes. In the preferred embodiment, where the device separates charged biopolymer fragments as rapidly as possible, the physical size is generally preferred to be as small as fabrication technologies permit and the intended separation medium allows. In this section, exemplary fabrication methods using standard microfabrication technologies are presented for device type I and II that are suitable for an aqueous separation medium with an applied potential difference of approximately 2 volts. These methods are exemplary, as this invention includes devices of other dimensions and fabrication according to other technologies.

The size of the exemplary device of types I and II is approximately 1 cm to 10 cm along the separation axis and approximately 1 cm to 10 cm transverse to the separation axis. The channels in the device are approximately 30–50 $\mu$m wide, 10 $\mu$m deep, and spaced apart every 100 $\mu$m, with a separation of approximately 50 $\mu$m between adjacent channels. The electrodes of each plurality are spaced apart approximately 20 $\mu$m, i.e., L=20 $\mu$m, and are approximately 0.8–1.0 $\mu$m wide. The electrodes of each plurality are relatively displaced by approximately their width, i.e., R=0.8–1.0 $\mu$m. The electrodes of each plurality are connected to electrode pads at the edges of the device for linking to an external voltage source.

Except where noted, the following microfabrication plans apply equally to devices of both types. The methods described are standard in the microfabrication art (Sze, 1988, *VLSI Technology*, McGraw Hill, New York).

5.5.1. Substrates

A preferred substrate for the device is glass, such as soda lime glass. Alternative substrates include fused silica, borosilicate, quartz, pyrex, and plastics such as polymethylmethacrylate, polycarbonate, polystyrene, polyimides, etc. The dimensions of the glass substrate are approximately 1–10 cm×1–10 cm, with a thickness of 1–5 mm. A suitable source for a glass substrate is a microscope slide of soda lime glass, for example a 75×50×1 mm slide (Fisher Scientific catalog No. 12-550C).

Prior to all other microfabrication steps, the substrate should be cleaned. For glass substrates, this can be done by immersing the substrates in a hot bath of $H_2SO_4/H_2O_2$, rinsing in $H_2O$ for 10 min, rinsing again with $H_2O$, and drying in an oven at ≈150° C. for 10 min to remove adsorbed water.

5.5.2. Electrode Fabrication

The electrodes for the device can be fabricated from various metals. Preferred metals are Al, Ag, Au, and Pt. Al is advantageous in that readily available CMOS foundries can be used, and disadvantageous in that it is more susceptible to electrolytic decomposition than is a noble metal. Alternative electrode fabrication methods for these metals are described: a first method using etching and suitable for all the preferred metals; a first alternative suitable for Pt, and a second alternative suitable for Au.

Figure 15:
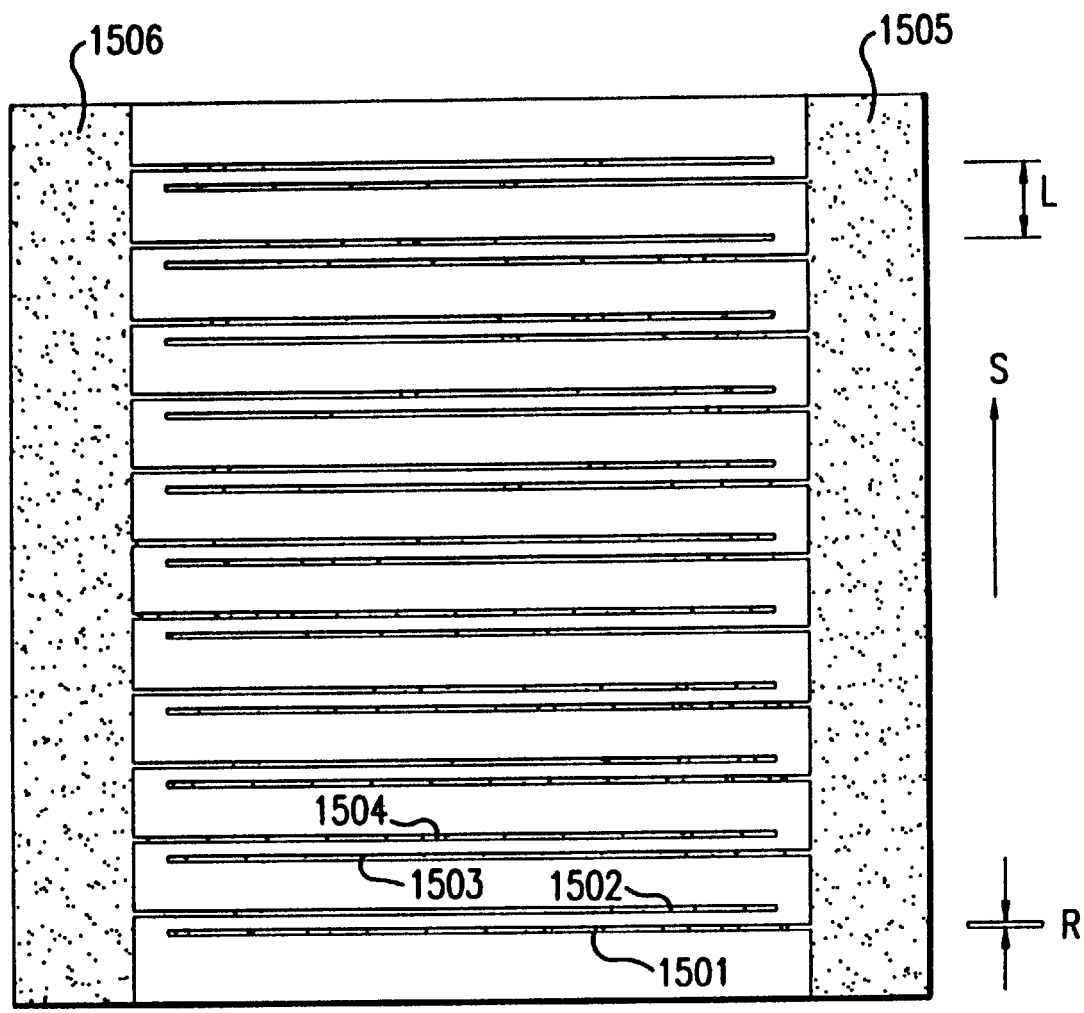
FIG. 15 illustrates an exemplary photolithography mask for the fabrication of electrodes for the device of FIG. 2.

Prior to electrode fabrication with the first method, or with the first alternative method, a patterning mask is produced for photolithography. FIG. 15 illustrates an exemplary mask. Electrodes, as at 1501, 1502, 1503 and 1504, are disposed substantially transversely to separation axis S. Each electrode is approximately 1 $\mu$m wide. The electrodes form two pluralities, electrodes of each plurality being connected to one of electrode pads 1505 and 1506. These pads are macroscale, approximately 0.1 mm, and serve as contact points to an external voltage source. Electrodes of each plurality are periodically spaced with distance L and are displaced with respect to each other with distance R. A mask of these dimension is readily constructed with standard microlithographic technology. For example, a suitable mask is obtained by selectively removing chrome deposited onto a quartz surface. The chrome is removed, for example, using computer aided design that provides input for a pattern generator. If obtainable, smaller feature sizes are preferable; the sizes used here are exemplary.

A first method for fabricating electrodes begins with depositing a uniform 1 $\mu$m thick layer of the selected metal on the side of the substrate which is to carry the electrodes. The metal can be deposited by, for example, physical vapor deposition, chemical vapor deposition, or sputtering. Then a positive photoresist is spin-coated on top of the layer of metal, and is stabilized by soft-baking. The features on the mask are transferred to the photoresist by irradiation with UV light, and the unprotected regions exposed to the light are dissolved by an appropriate solvent. The surviving photoresist is fixed in place by hard-baking at a high temperature.

The electrodes are generated by etching the region of metal unprotected by photoresist. For Al electrodes, the etching can be accomplished by exposing the surface to $Cl_2$ vapor. The $Cl_2$ molecules react with Al atoms on the surface to produce $AlCl_3$, which is volatile and leaves the surface. Wet etching is not preferable for Au and Ag electrodes because undercutting will destroy the $\mu$m-scale electrodes. These features are preferably etched using $Ar^+$ ion milling. In this method, $Ar^+$ ions from an Ar radio-frequency plasma are accelerated into the surface and cause etching by physical bombardment. Milling enables the electrodes to be produced with straight side-walls, preserving the mask dimensions.

After etching, the remaining photoresist is removed from the surface of the substrate and the surface carrying the electrodes is cleaned for subsequent processing.

A first alternative method suitable for Pt electrodes uses standard micromachining technologies. The fabrication begins with the deposition of a 10 nm thick Ti layer using an evaporation system. This Ti layer acts as an adhesion layer between the subsequent Pt layer and the glass. Next, a 100 nm thick layer of Pt is deposited on top of the Ti using an Ar ion sputtering system. The electrodes are defined in the metal layers using photolithography and etching. This process begins with spin-coating a photoresist on top of the Pt and exposing the photoresist with UV light through the photolithography mask that has the electrode pattern on it. The exposed areas of the photoresist can then be dissolved away in a developer to leave the unexposed regions that define the electrode pattern. The photoresist will protect the areas of the metal to be retained; the rest of the metal is removed using ion milling. In the milling process, positively charged $Ar^+$ ions are electrically accelerated to impinge on the surface of the metal and physically erode the layers. Once this etching is completed, the photoresist is dissolved with acetone to leave the finished electrodes.

Figure 16A:
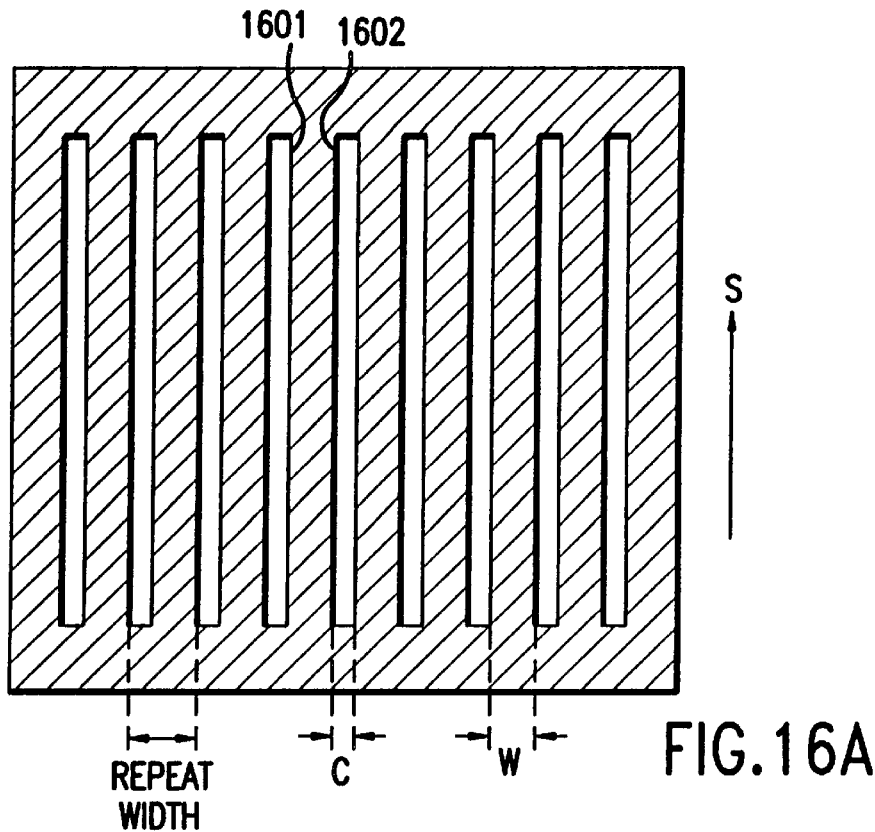
FIGS. 16A–16B illustrate an exemplary photolithography masks for the fabrication of channels for the device of FIG. 2.
Figure 16B:
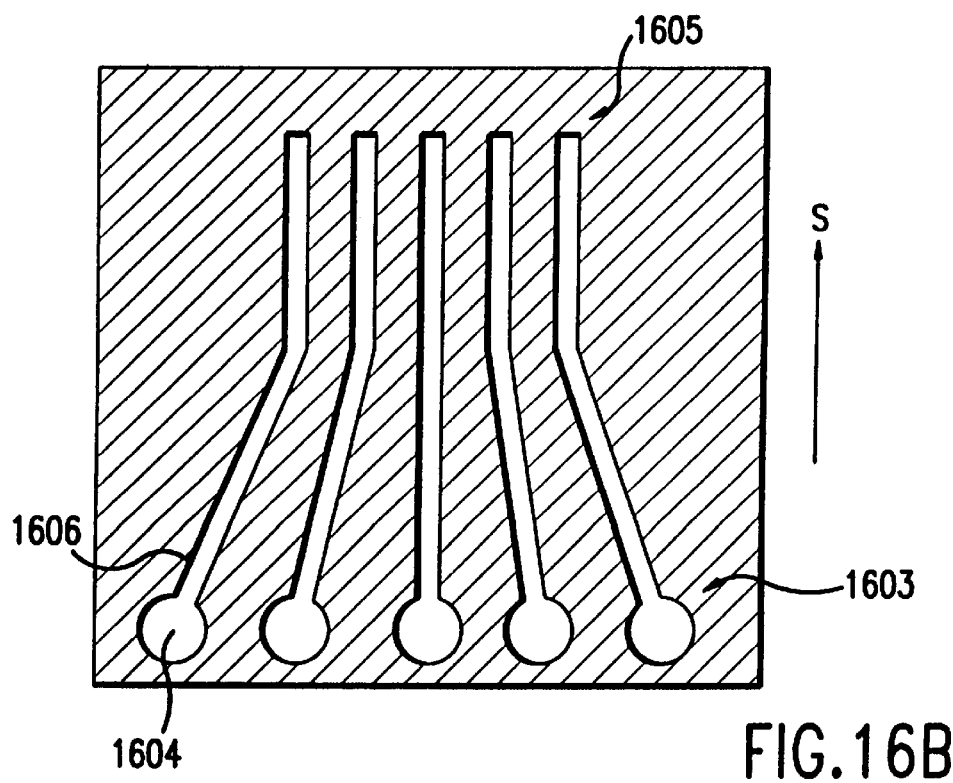

A second alternative method suitable for Au uses microcontact printing ($\mu$CP) (Xia et al., 1995, *J. Am. Chem. Soc.* 117:3274–3275; Jackman et al., 1995, *Science* 269:664–666). Instead of a photolithography mask, an elastomeric stamp made according to an identical pattern of the same dimensions is used. FIGS. 16A–B illustrate exemplary patterns. The stamp can be fabricated from polydimethylsiloxane. As before, Au is deposited to a thickness of 1 $\mu$m on the surface of the substrate using standard methods. Next, the elastomeric stamp is wetted with an alkanethiol and pressed against the gold surface. A suitable alkanethiol is $CH_3(CH_2)_{15}SH$ (Kumar et al., 1994, *Langmuir* 10:1498–1511). Controlled spreading of the patterned self-assembled alkanethiol monolayer on the gold surface can be achieved by performing the printing under water, which has the further benefit of shrinking the feature size in a predictable manner. The stamp and substrate are removed from the water and dried using $N_2$ gas, and then the stamp is removed from the substrate. Unprotected gold is removed by immersion in a cyanide solution (0.1M KCN, 1M KOH) with vigorous stirring using air or oxygen as an oxidant (Kumar et al., supra.). After a good rinse, the alkanethiol is removed from the surface to yield the pluralities of gold electrodes.

5.5.3. Device Type I Channel Fabrication

Device type I channels can be fabricated by wet-etching of a glass substrate. Prior to channel fabrication, a photolithography mask must be constructed. FIG. 16A illustrates an exemplary mask. The channels are defined by transparent bands, as at 1601 and 1602, on the otherwise opaque mask. Width C of each band is the desired channel width minus any expected undercutting during the etching process. For the process described, since the expected undercutting is 8–10 $\mu$m, 40 $\mu$m wide bands produce channels of the desired 55–60 $\mu$m final width. Width W between the bands is the desired channel spacing plus any expected undercutting.

FIG. 16B illustrates an alternate channel geometry. Here channels, such as channel 1606, converge from a wide spacing at a loading zone, indicated generally at 1603, to a narrow spacing at a detection zone, indicated generally at 1605. The wide spacing in loading zone 1603 allows the channels to accommodate injection ports, such as port 1604, of a diameter greater than the desired spacing between the channels. Although FIG. 16B illustrates piece-wise linear channels, alternative channel geometries, for example curvilinear, are adaptable to this invention.

A suitable photolithography mask may be fabricated by selectively removing chrome deposited onto a quartz surface. The chrome is removed, for instance, using a computer-generated design that serves as input to a pattern generator.

Channel fabrication begins with spin-coating a positive photoresist onto the glass substrate. A suitable photoresist is generated by exposing the substrate to hexamethyldisilazane vapor for 5 min, spin-coating with photoresist (Microposit S1400-31, Shipley, Newton, Mass.), and stabilizing the photoresist by heating at 90° C. for 0.5 hr. The mask is aligned over the coated glass substrate and the pattern is imprinted on the photoresist using UV light. The regions of photoresist exposed to the UV light are dissolved away (1:1 mixture of $H_2O$ and Microposit developer concentrate, Shipley), and the surviving photoresist is fixed by baking at 150° C. for 1 hr.

Alternately, the channels may be defined in the glass substrate using a Cr layer. This process starts with evaporating a 100 nm thick Cr layer onto the glass. The Cr layer over the lanes to be fabricated is then removed using photolithography and etching.

Next, the unprotected areas of the substrate are wet-etched by exposing the surface of the glass chip to an aqueous $NH_4/HF$ etching solution (1:1 mixture of BOE 5:1 and BOE 10:1, J. T. Baker, Phillipsburg, N.J.). Etching for 20 min produces channels 10–15 nm deep, and undercuts the photoresist 8–10 Mm on each side. The 40 $\mu$m feature size on the patterning mask therefore generates channels of the exemplary width of 55–60 $\mu$m. After etching, the photoresist or Cr layer is removed from the substrate, for example, in the case of glass, by cleaning with hot $H_2SO_4/H_2O_2$ as previously described.

5.5.4. Device Type II Channel Fabrication

Channels for device type II are preferably fabricated on top of the electrodes. Alternatively, they can be fabricated on top of the other substrate. A suitable photolithography mask is first fabricated. Such a mask is generally similar to that for the device type I channels with the three exceptions. First, the mask defines two channel walls banding each channel. Second, the channel wells are defined by transparent bands with the remainder of the mask being opaque (a negative mask). Third, as no undercutting is expected in this method, the mask dimensions should exactly match the intended channel and channel wall dimensions.

Then, the channels are fabricated by first spin-coating a UV-sensitive polyamide solution on top of the surface of the substrate to a depth of approximately 10 $\mu$m. The polyamide remains in place in the regions which are exposed to UV light, requiring that the photolithography mask be a negative image. The mask pattern is imprinted on the polyamide photoresist by illumination with UV light. The region of the polyamide layer under clear portions of the mask is stabilized by cross-linking due to the UV radiation. The remainder of the polyamide layer is dissolved with a suitable developer. The cross-linking forms a straight sidewall which is preserved during the developing and curing stages. Next, the glass chip is hard-baked at approximately 150° C. to set the polyamide layer. This completes the microfabrication of the channels.

5.5.5. Injection Port Fabrication

Injection ports may be fabricated in the substrate that does not carry the electrode pattern if desired. Holes for the injection ports can be fabricated by drilling either by a laser or a diamond tipped drill bit. Preferably, the drilled holes are sized to permit the injection of sample with a micropipette tip, so 500 $\mu$m is an adequate size. Since the preferable size of the injection ports is 5 to 10 times the preferable spacing between the channels, the converging channel pattern of FIG. 16B is preferable to the straight pattern of FIG. 16A for closely spaced channels in the migration and detection regions.

5.5.6. Fusing The Substrates

In order to create closed separation lanes in the device, the substrate with the channels and the other substrate must be bonded together. First, both sides are cleaned thoroughly and then are brought into contact. For device type I, the temperature is steadily increased to the annealing temperature of approximately 500°–600° C., where it is held for a few hours to ensure good bonding of the surfaces. For device type II, a flat silica plate is fused to the polyamide surface of the channels at a lower temperature of approximately 200° C.

6. EXAMPLES

6.1. Separation Of Single Stranded DNA

Using the preferred model of the invention described in Sec. 5.3, the behavior of a separation device is calculated. The following device design parameters are assumed: L=10 $\mu$m, R=1 $\mu$m, length 1 cm, a potential difference of 1 V, and an aqueous separation medium. A $t_{on}$=1 msec and a $t_{off}$=60 msec are calculated as optimum for providing 2 base resolution in separating 100 base ssDNA. The total separation time is 60 min. With these design and operational parameters, the behavior of the device is calculated for a mixture of ssDNA fragments of lengths 10, 20, 30, 40, 50, 60, 70, 80, 90, and 100 (known as a standard 10-base sequencing ladder available from Research Genetics, Hunstville, Al.).

Figure 17:
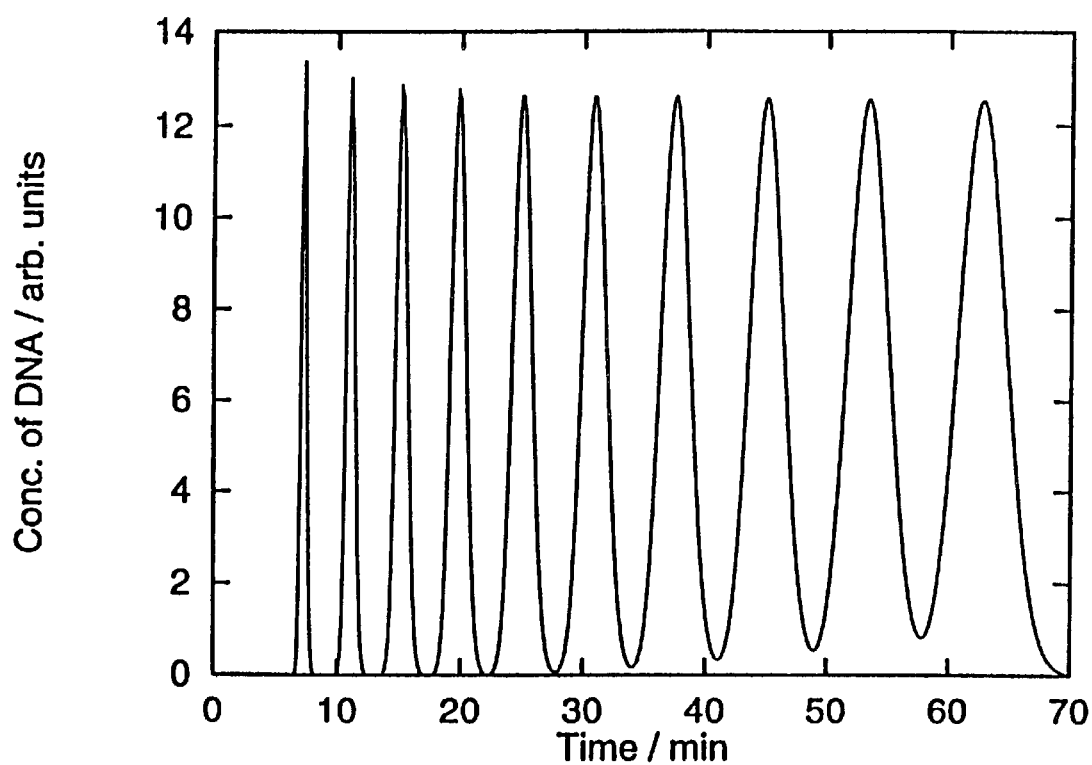
FIG. 17 illustrates an example of a hypothetical separation of DNA molecules according to the method of FIGS. 9A–9E.

FIG. 17 illustrates the predicted behavior of the device. The horizontal axis records increasing total separation time, and the vertical axis records the concentration of DNA exiting the device. The graph illustrates the predicted concentration of DNA exiting the device as a function of separation time. It is apparent that all the DNA fragments should be clearly separatable.

7. SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

8. COMPUTER PROGRAM FOR SELECTING OPTIMAL PARAMETERS /* calculate parameters for the dna separation device

```
                Copyright 1996 Curagen Corporation
*/
#include    <math.h>
#include    <stdio.h>
#include    <string.h>
#include    <stdlib.h>
#define     ABS(x)  ((x)>0?(x):(-(x)))
#define     PI 3.141592653589793 /* why not? */
#define     EBREAK 1.e4 /* breakdown field for water */
#define     MINLOG -6.
#define     MAXLOG 1.
/* erfc by polynomial approximation */
#define     A1  0.2548296
#define     A2  -0.28449674
#define     A3  1.4214137
#define     A4  -1.453152
#define     A5  1.0614054
#define     QP  0.3275911
#define
ERFC(x)( (((((A5*(1./(1.+QP*x))+A4)*(1./(1.+QP*x))+A3)*\
(1./(1.+QP*x))+A2)*(1./(1.+QP*x))+A1)*(1./(1.+Qp*x))*exp(-x*x))
double R,L; /* R is the small spacing, L is the well spacing*/
double alphafn(double d, double t)
{
double alpha,x;
x = R sqrt(4. * d * t);
alpha 0.5 * ERFC(x);
return(alpha);
}
main()
{
double n,dn; /* n and delta n */
int nstrand; /* 1 for ssDNA, 2 for dsDNA */
double d,d1; /* diffusivity for length n and (n + dn) */
double logt,t,alpha,alphal,dadn,dndasq,cycles,time;
double tbest, timebest,t_on,vO;
int ntmp;
double dtmp;
char line[100];
char *datafile = "data";
FILE *fp;
R = 1.;
L = 10.;
printf("Enter R (smaller spacing) and L (larger spacing) in microns: ");
fgets(line,sizeof(line),stdin);
sscanf(line,"%1f %1f",&R,&L);
R *= 1.e-4; /* convert to cm*/
L *= 1.e-4;
printf ("Device size: R = %lf microns, L = %lf microns\n", R*1.e4,L*1.e4);
/*
    the breakdown field of water is 1e4 V/cm
    choose VO so 2VO/r = 1e4 V/cm
    */
vO + R * EBREAK / 2.;
/*
    use a maximum overpotential of 2VO = 1 V to avoid electrolysis
8/
if (vO > 0.5) { vO = 0.5;
printf("V_O = %1f V, generating maximum field of %1f V/cm\n", vO,2.*vO/R);
printf("N = the length of the sequence\n"
"Delta N = the resolution (1 for sequencing)\n")
while (1) {
printf("Enter N and Delta N: ");
fgets(line,sizeof(line),stdin);
sscanf(line,"%lf %lf",&n,&dn);
if (n < 1) { break;}
printf("Enter 1 for ssDNA or 2 for dsDNA: ");
fgets(line,sizeof(line),stdin);
sscanf (line, "%d",&nstrand);
if ((nstrand!=1)&&(nstrand!=2)) { break; }
fp = fopen(datafile,"W") ;
/* determine the diffusion constants for n and n+1 units
are cm-2/sec
t-on is the relaxation time for a 200 V potential
*/
if (nstrand == 1) {
t_on (L-R)*(L-R)*2.24e-4/(R*pow((double) n,0.41));
t_on *= 1.e4; /* convert from cm to microns */
}
else {
t_on (L-R)*(L-R)*1.12e-4/R;
t_on 1.e4; /* convert from cm to microns */
}
printf("t-on + %1f s\n",t_on);
if (nstrand == 1) {
d = 1.14e-6 * pow(n, -0.59);
d1 = 1.14e-6 * pow(n+dn, -0.59);
}
else {
d = 1.14e-6 / n;
d1 = 1.14e-6 (n+dn);
}
tbest = 0.; timebest = 1.e100;
for (logt = MINLOG; logt <= MAXLOG; logt += 0.001) {
```

```
t = pow(10.,logt);
alpha = alphafn(d,t);
alpha1 = alphafn(dl,t);
dadn = alpha1 - alpha;
if (ABS(dadn) < 1.e-6) {continue;}
dndasq = 1. / (dadn * dadn);
cycles = alpha * (1. - alpha) * dndasq;
time = cycles * (t + t_on);
fprintf(fp,"%lf %lf %lf %lf %lf %15.10lf\n",
t,time/60.,cycles,alpha,dndasq,dadn);
if (time < timebest) { tbest = t; timebest = time;}
if (time > 10.*timebest) {break;}
}
fclose(fp);
t = tbest;
alpha = alphafn(d,t);
alpha1 = alphafn(d1,t);
dadn = alpha1 - alpha;
dndasq = 1. / (dadn * dadn);
cycles = alpha * (1. alpha) dndasq;
time = cycles * (t+t_on);
printf(" N %d Delta %d nstrand %d R (um) %lf L (um) %lf\n",
(int)n,(int)dn,nstrand,1.e4*R,1.e4*L);
printf(" t_on %g vO %g\n",t_on,vO);
printf("\nN = %d +/- %d\n"
"time (min) %lf\n"
"length (cm) %lf\n"
"t_off(sec) %lf\n"
"N_cyc %f \n"
"alpha %lf\n\n",
(int)n,(int)dn,
time/60.,alpha*cycles*L,t,cycles,alpha);
printf("%lf %lf\n",1.e4*L,alpha*cycles*L);
printf("%lf %lf\n",t+t-on,time/60.);
for (ntmp = 10; ntmp <= 100; ntmp += 10) {
dtmp = 1.14e-6 * pow(ntmp, -0.59);
printf("%d %lf\n",ntmp,alphafn(dtmp,t));
}
printf("End of program.\n");
}
```

What is claimed is:

1. A method for separating charged particles along a direction of separation in a separation medium comprising exposing said charged particles in said separation medium to an electric potential having spatial and temporal variations, said spatial variations of said electric potential comprising a plurality of electric potential wells for said charged particles disposed along said direction of separation, wherein each said electric potential well for said charged particles has a minimum to which said charged particles are attracted and which is eccentrically disposed with respect to adjacent maximums so that said minimum is closer to the adjacent maximum in said direction of separation than it is to others of the adjacent maximums in other directions, and said temporal variations of said electric potential comprising repeated alternations between at least three conditions, a first on-condition in which the charged particles are attracted to the minimums of said potential wells, a second condition in which the potential minimums are narrower and deeper than in said on-condition, and a third off-condition in which the charred particles can diffuse in said separation medium.

2. A method for separating charged particles along a direction of separation in a separation medium comprising exposing said charged particles in said separation medium to an electric potential having spatial and temporal variations, said spatial variations of said electric potential comprising a plurality of electric potential wells for said charged particles disposed along said direction of separation, wherein each said electric potential well for said charged particles has a minimum to which said charged particles are attracted and which is eccentrically disposed with respect to adjacent maximums so that said minimum is closer to the adjacent maximum in said direction of separation than it is to others of the adjacent maximums in other directions, and said temporal variations of said electric potential comprising repeated alternations between at least three conditions, a first on-condition in which the charged particles are attracted to the minimums of said potential wells, a second condition which is interspersed one or more times during said on-condition and in which the potential is reversed for a brief pulse duration sufficient to affect substantially only highly mobile counterions, and a third off-condition in which the charged particles can diffuse in said separation medium.

3. A method for separating charged particles along a direction of separation in a separation medium comprising exposing said charged particles in said separation medium to an electric potential having spatial and temporal variations, said spatial variations of said electric potential comprising a plurality of electric potential wells for said charged particles disposed along said direction of separation, wherein each said electric potential well for said charged particles has a minimum to which said charged particles are attracted and which is eccentrically disposed with respect to adjacent maximums so that said minimum is closer to the adjacent maximum in said direction of separation than it is to others of the adjacent maximums in other directions, and said temporal variations of said electric potential comprising repeated variations between at least two conditions, an on-condition in which the charged particles are attracted to the minimums of said potential wells and an off-condition in which the charged particles can diffuse in said separation medium, said off-condition being of a duration such that some of the charged particles can diffuse across more than one potential well.

4. A method for separating charged particles along a direction of separation in a separation medium comprising exposing said charred particles in said separation medium to an electric potential having spatial and temporal variations, said spatial variations of said electric potential comprising a plurality of electric potential wells for said charged particles disposed along said direction of separation, wherein each said electric potential well for said charged particles has a minimum to which said charged particles are attracted and which is eccentrically disposed with respect to adjacent maximums so that said minimum is closer to the adjacent maximum in said direction of separation than it is to others of the adjacent maximums in other directions, and said temporal variations of said electric potential comprising repeated variations between at least two conditions, an on-condition in which the charged particles are attracted to the minimums of said potential wells and an off-condition in which the charged particles can diffuse in said separation medium, said temporal variations having a frequency which changes during the separation of the charged particles.

5. A method for separating charged particles along a direction of separation in a separation medium comprising:

(a) exposing said charged particles in said separation medium to an electric potential having spatial and temporal variations, said spatial variations of said electric potential comprising a plurality of electric potential wells for said charged particles disposed along said direction of separation, wherein each said electric potential well for said charged particles has a minimum to which said charged particles are attracted and which is eccentrically disposed with respect to adjacent maximums so that said minimum is closer to the adjacent maximum in said direction of separation than it is to others of the adjacent maximums in other directions and said temporal variations of said electric potential comprising repeated variations between at least two conditions, an on-condition in which the charged particles are attracted to the minimums of said potential wells and an off-condition in which the charged particles can diffuse in said separation medium; and (b) attracting and trapping the charged particles in a loading zone potential well which attracts and traps the charged particles after loading and prior to exposing the charged particles to said varying electric potential.

6. A device for separating charged particles comprising:

(a) one or more separation lanes; and (b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, wherein said time-varying amplitude of said electric potential comprises repeated variations between at least two conditions, an on-condition in which said charged particles are attracted to said minimums and an off-condition in which said charged particles can diffuse in said separation medium, and wherein each said potential well has a spatial size, L, along said direction of separation, and wherein said potential minimum of each said potential well is disposed at a distance, R, from the nearest said adjacent potential maximum in said direction of separation, wherein R is selected to minimize the total separation time, $T_{tot}$, of the charged particles.

7. A device for separating charged particles comprising:

(a) one or more separation lanes; and (b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, wherein said time-varying amplitude of said electric potential comprises repeated variations between at least two conditions, an on-condition in which said charged particles are attracted to said minimums and an off-condition in which said charged particles can diffuse in said separation medium, and wherein each said potential well has a spatial size, L, along said direction of separation, and wherein said potential minimum of each said potential well is disposed at a distance, R, from the nearest said adjacent potential maximum in said direction of separation, wherein L and R are those distances which minimize the total separation time, $T_{tot}$, subject to constraints on minimum sizes that can be fabricated in a selected fabrication technology and to constraints on maximum potentials that can be applied in said separation medium.

8. A device for separating charged particles comprising:

(a) one or more separation lanes; and (b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, wherein said time-varying amplitude of said electric potential comprises repeated variations between at least two conditions, an on-condition in which said charged particles are attracted to said minimums and an off-condition in which said charged particles can diffuse in said separation medium, and wherein each said potential well has a spatial size, L, along said direction of separation, and wherein said potential minimum of each said potential well is disposed at a distance, R, from the nearest said adjacent potential maximum in said direction of separation, wherein R/L is selected to be less than approximately 0.3.

9. A device for separating charged particles comprising:

(a) one or more separation lanes;

(b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, and wherein said time-varying amplitude of said electric potential comprises repeated variations between at least two conditions, an on-condition in which said charged particles are attracted to said minimums and an off-condition in which said charged particles can diffuse in said separation medium; and (c) a separation medium configured as a slab, and wherein said slab of said separation medium functions as said one or more separation lanes.

10. A device for separating charged particles comprising:

(a) one or more separation lanes;

(b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, and wherein said time-varying amplitude of said electric potential comprises repeated variations between at least two conditions, an on-condition in which said charged particles are attracted to said minimums and an off-condition in which said charged particles can diffuse in said separation medium;

(c) one or more passages having bounded cross-sections and wherein each of said one or more separation lanes is in one of said one or more passages; and (d) a first and a second substrate, each said passage being bounded by said first substrate, by said second substrate, and by channel walls deposited on the surface of said second substrate.

11. A device for separating charged particles comprising:

(a) one or more separation lanes;

(b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, and wherein said time-varying amplitude of said electric potential comprises repeated variations between at least two conditions, an on-condition in which said charged particles are attracted to said minimums and an off-condition in which said charged particles can diffuse in said separation medium; and (c) one or more passages having bounded cross-sections, wherein said one or more passages converge from a broad spacing at one end of said one or more passages to a narrow spacing at the other end of said one or more passages, and wherein each of said one or more separation lanes is in one of said one or more passages.

12. A device for separating charged particles comprising:

(a) one or more separation lanes;

(b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, and wherein said time-varying amplitude of said electric potential comprises repeated variations between at least two conditions, an on-condition in which said charged particles are attracted to said minimums and an off-condition in which said charged particles can diffuse in said separation medium; and (c) one or more loading ports, each loading port in communication with one of the said one or more separation lanes and adapted to receive charged particles for loading into said one separation lane, said one or more loading ports being in a loading zone, and said one or more separation lanes converging in said direction of separation from a spacing sufficient to accommodate fluid communication with said one or more separation ports in said loading zone to a more close spacing.

13. A device for separating charged particles comprising:

(a) one or more separation lanes;

(b) a plurality of electrodes disposed for generating an electric potential well in said one or more separation lanes, said electric potential well having a stationary spatial pattern with a time-varying amplitude, wherein said stationary spatial pattern of said electric potential comprises a plurality of electric potential wells for said charged particles disposed in said one or more separation lanes, each said electric potential for said charged particles having a minimum to which said charged particles are attracted and which is eccentrically disposed with respect to adjacent maximums so that said minimum is closer to the adjacent maximum in a direction of separation oriented along said one or more separation lanes than it is to others of the adjacent maximums in other directions, and wherein said time-varying amplitude of said electric potential comprises repeated variations between at least two conditions, an on-condition in which said charged particles are attracted to said minimums and an off-condition in which said charged particles can diffuse in said separation medium; and (c) means for thermal control of a separation medium in said one or more separation lanes.

14. A device for separating charged particles comprising:

(a) one or more separation lanes; and (b) a plurality of electrodes disposed for generating an electric potential in said one or more separation lanes, said electric potential having a stationary spatial pattern with a time-varying amplitude, said spatial pattern of said electric potential being of a substantially saw-tooth form, wherein said substantially saw-tooth form comprises a plurality of electric potential wells for said charged particles disposed in said one or more separation lanes, each said electric potential well having a minimum to which said charged particles are attracted and which is eccentrically disposed with respect to adjacent maximums in a direction oriented alone said one or more separation lanes so that said minimum is closer to the adjacent maximum along said direction than it is to others of the adjacent electric potential maximums in other directions, and wherein said time-varying amplitude of said electric potential comprises repeated variations between at least two conditions, an on-condition in which said charged particles are attracted to said minimums and an off-condition in which said charged particles can diffuse in said separation medium, wherein said plurality of electrodes comprises a first sub-plurality and a second sub-plurality of electrodes, wherein electrodes of each sub-plurality are substantially periodically spaced apart with a distance of approximately L, and wherein the first and second sub-pluralities of electrodes are interdigitated with an offset of approximately R with R/L being less than approximately 0.3.

15. A device for separating charged particles comprising:
(a) one or more separation lanes; and
(b) a plurality of electrodes disposed for generating an electric potential in said one or more separation lanes, said electric potential having a stationary spatial pattern with a time-varying amplitude, said spatial pattern of said electric potential being of a substantially saw-tooth form, wherein said substantially saw-tooth form comprises a plurality of electric potential wells for said charged particles disposed in said one or more separation lanes, each said electric potential well having a minimum to which said charged particles are attracted and which is eccentrically disposed with respect to adjacent maximums in a direction oriented alone said one or more separation lanes so that said minimum is closer to the adjacent maximum along said direction than it is to others of the adjacent electric potential maximums in other directions, and wherein said time-varying amplitude of said electric potential comprises repeated variations between at least two conditions, an on-condition in which said charged particles are attracted to said minimums and an off-condition in which said charged particles can diffuse in said separation medium, wherein said plurality of electrodes comprises a first sub-plurality and a second sub-plurality of electrodes, wherein electrodes of each sub-plurality are substantially periodically spaced apart with a distance of approximately L, and wherein the first and second sub-pluralities of electrodes are interdigitated with an offset of approximately R, said electrodes further comprising a third sub-plurality of electrodes, said third sub-plurality interdigitated with and offset form said first and said second sub-pluralities of electrodes, and said pluralities of electrodes being capable of generating at the position of each said saw-tooth shaped potential well a narrower and deeper potential minimum than present without said third sub-plurality.

16. A device for separating charged particles comprising:
(a) one or more separation lanes;
(b) a plurality of electrodes disposed for generating an electric potential in said one or more separation lanes, said electric potential having a stationary spatial pattern with a time-varying amplitude, said spatial pattern of said electric potential being of a substantially saw-tooth form, wherein said substantially saw-tooth form comprises a plurality of electric potential wells for said charged particles disposed in said one or more separation lanes, each said electric potential well having a minimum to which said charged particles are attracted and which is eccentrically disposed with respect to adjacent maximums in a direction oriented alone said one or more separation lanes so that said minimum is closer to the adjacent maximum along said direction than it is to others of the adjacent electric potential maximums in other directions, and wherein said time-varying amplitude of said electric potential comprises repeated variations between at least two conditions, an on-condition in which said charged particles are attracted to said minimums and an off-condition in which said charged particles can diffuse in said separation medium; and (c) means for thermal control of a separation medium in said one or more separation lanes.

17. A device for separating charged particles along a direction of separation comprising:
(a) means for containing a separation medium in one or more separation lanes oriented along said direction of separation;
(b) means for generating an electric potential in said one or more separation lanes having a stationary spatial pattern with a time-varying amplitude, wherein said stationary spatial pattern of said electric potential comprises a plurality of electric potential wells for said charged particles disposed in said one or more separation lanes, each said electric potential well for said charged particles having a minimum to which said charged particles are attracted and which is eccentrically disposed with respect to adjacent maximums so that said minimum is closer to the adjacent maximum in said direction of separation than it is to others of the adjacent maximums in other directions, and wherein said time-varying amplitude of said electric potential comprises repeated variations between at least two conditions, an on-condition in which said charged particles are attracted to said minimums and an off-condition in which said charged particles can diffuse in said separation medium; and (c) means for thermal control of a separation medium in said one or more separation lanes.

18. A method for separating charged particles along a direction of separation comprising:
(a) loading into a separation medium at least two types of charged particles, said two types of charged particles having different diffusivities in said separation medium; and
(b) exposing the charged particles in said separation medium to an electric potential having a stationary spatial pattern with a time-varying amplitude, wherein said stationary spatial pattern of said electric potential comprises a plurality of electric potential wells for said charged particles disposed along said direction of separation, each said electric potential well for said charged particles having a minimum to which said charged particles are attracted and which is eccentrically disposed with respect to adjacent maximums so that said minimum is closer to the adjacent maximum in said direction of separation than it is to others of the adjacent maximums in other directions, and said time-varying amplitude of said electric potential comprising repeated variations between at least two conditions, an on-condition in which the charged particles are attracted to said minimums and an off-condition in which the charged particles can diffuse in said separation medium;

(c) selecting the duration of said on-condition, $t_{on}$, to be the approximately least time sufficient to attract substantially all charged particles within each said potential well into said potential well into said potential minimum of said potential well; and (d) selecting the duration of said off-condition, $t_{off}$, to be approximately the time which minimizes the total time, $T_{tot}$, required for said at least two types of charged particles to be separated sufficiently to be observationally distinguished, wherein said $T_{tot}$ is determined by solving equations describing the diffusion of the charged particles in said electric potential and equations describing generation of said electric potential.

19. A method for separating charged particles along a direction of separation comprising:

(a) loading into a separation medium at least two types of charged particles, said two types of charged particles having different diffusivities in said separation medium; and (b) exposing the charged particles in said separation medium to an electric potential having a stationary spatial pattern with a time-varying amplitude, wherein said stationary spatial pattern of said electric potential comprises a plurality of electric potential wells for said charged particles disposed along said direction of separation, each said electric potential well for said charged particles having a minimum to which said charged particles are attracted and which is eccentrically disposed with respect to adjacent maximums so that said minimum is closer to the adjacent maximum in said direction of separation than it is to others of the adjacent maximums in other directions, and said time-varying amplitude of said electric potential comprising repeated variations between at least two conditions, an on-condition in which the charged particles are attracted to said minimums and an off-condition in which the charged particles can diffuse in said separation medium;

(c) selecting the duration of said on-condition, $t_{on}$, to be the approximately least time sufficient to attract substantially all charged particles within each said potential well into said potential well into said potential minimum of said potential well; and (d) selecting the duration of said off-condition, $t_{off}$, to be approximately the time which minimizes the total time, $t_{tot}$, required for said at least two types of charged particles to be separated sufficiently to be observationally distinguished, wherein said $t_{off}$ systematically increases or decreases during said separation of the charged particles.

20. A method for separating charged particles along a direction of separation comprising:

(a) loading into a separation medium at least two types of charged particles, said two types of charged particles having different diffusivities in said separation medium; and (b) exposing the charged particles in said separation medium to an electric potential having a stationary spatial pattern with a time-varying amplitude, wherein said stationary spatial pattern of said electric potential comprises a plurality of electric potential wells for said charged particles disposed along said direction of separation, each said electric potential well for said charged particles having a minimum to which said charged particles are attracted and which is eccentrically disposed with respect to adjacent maximums so that said minimum is closer to the adjacent maximum in said direction of separation than it is to others of the adjacent maximums in other directions, and said time-varying amplitude of said electric potential comprises repeated variations between at least two conditions, an on-condition in which the charged particles are attracted to said minimums and an off-condition in which the charged particles can diffuse in said separation medium, wherein each said potential well has a spatial size, L, along said direction of separation, and wherein said potential minimum of each said potential well is situated at a distance, R, from the nearest adjacent potential maximum with R/L being less than approximately 0.3.

21. A method for separating charged particles along a direction of separation comprising:

(a) loading into a separation medium at least two types of charged particles, said two types of charged particles having different diffusivities in said separation medium; and (b) exposing the charged particles in said separation medium to an electric potential having a stationary spatial pattern with a time-varying amplitude, wherein said stationary spatial pattern of said electric potential comprises a plurality of electric potential wells for said charged particles disposed along said direction of separation, each said electric potential well for said charged particles having a minimum to which said charged particles are attracted and which is eccentrically disposed with respect to adjacent maximums so that said minimum is closer to the adjacent maximum in said direction of separation than it is to others of the adjacent maximums in other directions, and said time-varying amplitude of said electric potential comprises repeated variations between at least two conditions, an on-condition in which the charged particles are attracted to said minimums and an off-condition in which the charged particles can diffuse in said separation medium, wherein each said potential well has a spatial size, L, along said direction of separation, and wherein said potential minimum of each said potential well is situated at a distance, R, from the nearest adjacent potential maximum, R being selected to minimize the total time, $T_{tot}$, required for said at least two types of charged particles to be separated sufficiently to be observationally distinguished.

22. A method for separating charged particles along a direction of separation comprising:

(a) loading into a separation medium at least two types of charged particles, said two types of charged particles having different diffusivities in said separation medium; and (b) exposing the charged particles in said separation medium to an electric potential having a stationary spatial pattern with a time-varying amplitude, wherein said stationary spatial pattern of said electric potential comprises a plurality of electric potential wells for said charged particles disposed along said direction of separation, each said electric potential well for said charged particles having a minimum to which said charged particles are attracted and which is eccentrically disposed with respect to adjacent maximums so that said minimum is closer to the adjacent maximum in said direction of separation than it is to others of the adjacent maximums in other directions, and said time-varying amplitude of said electric potential comprises repeated variations between at least two conditions, an on-condition in which the charged particles are attracted to said minimums and an off-condition in which the charged particles can diffuse in said separation medium, wherein each said potential well has a spatial size, L, along said direction of separation, and wherein said potential minimum of each said potential well is situated at a distance, R, from the nearest adjacent potential maximum, with L and R selected according to a simultaneous optimization to minimize the total time $T_{tot}$ subject to constraints on minimum sizes that can be fabricated in a selected fabrication technology and to constraints on maximum potentials that can be applied in said separation medium.

23. The method according to claim 22 wherein said simultaneous optimization systematically varies R from a minimum value determined by said minimum size constraints in order to find the minimum value of $T_{tot}$.

24. A device for separating charged particles comprising:
(a) a substantially flat first substrate having on one surface one or more channels of greater length dimension than cross-sectional dimensions;
(b) a substantially flat second substrate juxtaposed to said first substrate such that said one or more channels form one or more separation lanes;
(c) a first and a second electrode pad; and
(d) a plurality of electrodes disposed for generating an electric potential in said one or more separation lanes and which are configured to be substantially linear and substantially transverse to said one or more separation lanes, and wherein said plurality of electrodes comprises a first sub-plurality and a second sub-plurality of electrodes, wherein electrodes of each sub-plurality are substantially periodically spaced apart with a distance of approximately L, wherein the first and second sub-pluralities of electrodes are inter-digitated with an offset of approximately R, and wherein electrodes of said first sub-plurality are in electrical contact with said first electrode pad and wherein electrodes of said second sub-plurality are in electrical contact with said second electrode pad, and wherein R/L is less than 0.5, whereby said electric potential generated in said one or more separation lanes by said plurality of electrodes has a substantially eccentric saw-tooth shape, wherein said substantially eccentric saw-tooth shape comprises a plurality of electric potential wells for said charged particles disposed in said one or more separation lanes, each said electric potential well for said charged particleS having a minimum to which said charged particles are attracted and which is eccentrically disposed with respect to adjacent maximums so that said minimum is closer to the adjacent maximum in a direction oriented along said one or more separation lanes than it is to others of the adjacent maximums in other directions.

25. The device according to claim 24 wherein said length dimension of said one or more separation lanes is less than approximately 10 cm and wherein said cross-sectional dimensions of said one or more separation lanes are less than approximately 100 $\mu$m.

26. The device according to claim 24 wherein R/L is less than approximately 0.3.

27. The device according to claim 24 wherein L is less than approximately 100 $\mu$m and wherein R is less than approximately 30 $\mu$m.

28. The device according to claim 24 further comprising means for loading the charged particles in said one or more separation lanes.

29. The device according to claim 24 further comprising means for detecting any labels on the charged particles, situated so as to detect the labels after separation of the charged particles within the separation lanes.

30. The device according to claim 24 further comprising means for thermal control of a separation medium in said one or more separation lanes.

31. A device for separating charged particles comprising:
(a) a substantially flat first substrate;
(b) a substantially flat second substrate to which the first substrate is juxtaposed;
(c) a plurality of channel walls fabricated on the surface of said second substrate such that one or more separation lanes having a greater length dimension than cross-sectional dimensions are formed by the juxtaposition of said first substrate to said second substrate;
(d) a first and a second electrode pad; and
(e) a plurality of electrodes disposed for generating an electric potential in said one or more separation lanes and which are configured to be substantially linear and substantially transverse to said one or more separation lanes, and wherein said plurality of electrodes comprises a first sub-plurality and a second sub-plurality of electrodes, wherein electrodes of each sub-plurality are substantially periodically spaced apart with a distance of approximately L, wherein the first and second sub-pluralities of electrodes are inter-digitated with an offset of approximately R, and wherein electrodes of said first sub-plurality are in electrical contact with said first electrode pad and wherein electrodes of said second sub-plurality are in electrical contact with said second electrode pad, and wherein R/L is less than 0.5, whereby said electric potential generated in said one or more separation lanes by said plurality of electrodes has a substantially eccentric saw-tooth shape, wherein said substantially eccentric saw-tooth shape comprises a plurality of electric potential wells for said charged particles disposed in said one or more separation lanes, each said electric potential well for said charged particleS having a minimum to which said charged particles are attracted and which is eccentrically disposed with respect to adjacent maximums so that said minimum is closer to the adjacent maximum in a direction oriented along said one or more separation lanes than it is to others of the adjacent maximums in other directions.

32. The device according to claim 31 wherein said length dimension of said one or more separation lanes is less than approximately 10 cm and wherein said cross-sectional dimensions of said one or more separation lanes are less than approximately 100 $\mu$m.

33. The device according to claim 31 wherein R/L is less than approximately 0.3.

34. The device according to claim 31 wherein L is less than approximately 100 μm and wherein R is less than approximately 30 μm.

35. The device according to claim 31 further comprising means for loading the charged particles in said one or more separation lanes.

36. The device according to claim 31 further comprising means for detecting any labels on the charged particles, situated so as to detect the labels after separation of the charged particles within the separation lanes.

37. The device according to claim 31 further comprising means for thermal control of a separation medium in said one or more separation lanes.

38. A method for separating charged particles along a direction of separation in a separation medium comprising:

(a) inputting diffusivities of the charged particles and one or more electrical breakdown parameters of the separation medium;

(b) calculating a first optimum time for an on-condition of an electric potential, wherein said electric potential has a stationary spatial pattern with a time-varying amplitude, said stationary spatial pattern of said electric potential comprising a plurality of electric potential wells for said charged particles disposed along said direction of separation, each said electric potential well for said charged particles having a minimum to which said charged particles are attracted and which is eccentrically disposed with respect to adjacent maximums so that said minimum is closer to the adjacent maximum in said direction of separation than it is to others of the adjacent maximums in other directions, and wherein said electric potential has a time-varying amplitude comprising repeated variations between at least two conditions, said on-condition in which said charged particles are attracted to said minimums and an off-condition in which the charged particles can diffuse in said separation medium;

(c) calculating a second optimum time for said off-condition of said electric potential as the time that minimizes a total separation time of the charged particles; and (d) exposing said charged particles in said separation medium to said electric potential having said spatial pattern with said time-varying amplitude.

39. The method according to claim 38 wherein the charged particles are DNA molecules and said inputting step comprises inputting the lengths of the DNA molecules and calculating the diffusivities of the DNA molecules from said input lengths.

40. The method according to claim 38 where said step of calculating said first optimum time comprises calculating the least time sufficient to attract substantially all charged particles within each said potential well into said potential minimum of said potential well, said least time determined according to a model in which the charged particles migrate with velocities in said separation medium that are directly proportional to the charges of the charged particles, the electric field in said potential wells, and said diffusivities of the charged particles.

41. The method according to claim 38 wherein said step of calculating said second optimum time comprises calculating said total separation time according to a model in which each charged particle undergoes during separation a random walk between said potential wells, and wherein the probability that a charged particle undergoes a random step from one of said wells to another of said wells is given by the probability that said charged particle diffuses from the potential minimum of said one of said wells to the nearest potential maximum of said another of said wells during said off-condition.

42. The method according to claim 38 wherein said step of calculating said second optimum time comprises calculating said total separation time by solving equations describing the diffusion of the charged particles in said electric potential and equations describing generation of said electric potential.

43. The method according to claim 38 wherein said step of calculating said second optimum time of said off-condition comprises systematically increasing the time of said off-condition from a minimum value in order to find the minimum value of the total separation time.

44. The method according to claim 38 wherein each said potential well has a spatial size, L, along said direction of separation, wherein said potential minimum of each said potential well is situated at a distance, R, from the nearest adjacent potential maximum, and further comprising calculating a value for R that minimizes the total separation time.

45. The method according to claim 38 wherein each said potential well has a spatial size, L, along said direction of separation, wherein said potential minimum of each said potential well is situated at a distance, R, from the nearest adjacent potential maximum, and further comprising calculating values for L and R that minimize the total separation time.

46. The method according to claim 45 wherein said simultaneous optimization systematically increases R from a minimum value in order to find the minimum value of the total separation time.

* * * * *